United States Patent
Hardwick et al.

(10) Patent No.: US 6,570,002 B1
(45) Date of Patent: May 27, 2003

(54) INHIBITOR OF PROGRAMMED CELL DEATH

(75) Inventors: J. Marie Hardwick, Baltimore, MD (US); Emily H. Cheng, St. Louis, MO (US); B. Nelson Chau, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 09/512,346

(22) Filed: Feb. 24, 2000

Related U.S. Application Data

(60) Provisional application No. 60/122,104, filed on Feb. 26, 1999.

(51) Int. Cl.[7] .............................................. C07H 21/02
(52) U.S. Cl. ..................................................... 536/23.1
(58) Field of Search ............................... 536/23.1, 23.5

(56) References Cited

U.S. PATENT DOCUMENTS

| | | |
|---|---|---|
| 5,686,595 A | 11/1997 | Reed et al. |
| 5,770,443 A | 6/1998 | Kiefer et al. |
| 5,834,209 A | 11/1998 | Korsmeyer |
| 5,834,309 A | 11/1998 | Thompson et al. |
| 5,858,678 A | 1/1999 | Chinnadurai |
| 5,858,715 A | 1/1999 | Hillman et al. |

OTHER PUBLICATIONS

Cheng et al.; "Bax–independent inhibition of apoptosis by Bcl–$x_L$"; Nature, vol. 379, Feb. 8, 1996, pp. 554–556.

Cheng et al.; "Conversion of Bcl–2 to a Bax–like Death Effector by Caspases"; Science, vol. 278, Dec. 12, 1997, pp. 1966–1968.

Cheng et al.; "A Bcl–2 homolog encoded by Kaposi sarcoma–associated virus, human herpesvirus 8, inhibits apoptosis but does not heterodimerize with Bax or Bak"; Proc. Natl. Acad. Sci. USA, vol. 94, Jan. 1997, pp. 690–694.

Clem et al.; "Modulation of cell death by Bcl–$x_L$ through caspase interaction"; Proc. Natl. Acad. Sci. USA, vol. 95, Jan. 1998, pp. 554–559.

Kirsch et al.; Caspase–3–dependent Cleavage of Bcl–2 Promotes Release of Cytochrome c*; The Journal of Biological Chemistry, vol. 274, No. 30, Issue of July 23, pp. 21155–21161, 1999.

Lewis et al.; "Inhibition of virus–induced neuronal apoptosis by Bax"; Nature Medicine, vol. 5, No. 7, Jul. 1999, pp. 832–835.

Susin et al.; "Mitochondrial Release of Caspase–2 and –9 during the Apoptotic Prcess"; J. Exp. Med., vol. 189, No. 2, Jan. 18, 1999, pp. 381–393.

Chang et al.; "Identification of a novel regulatory domain in Bcl–$x_L$ and Bcl–2"; The EMBO Journal, vol. 16, No. 5, 1997, pp. 968–977.

(List continued on next page.)

*Primary Examiner*—Sheela Huff
(74) *Attorney, Agent, or Firm*—Dickstein Shapiro Morin & Oshinsky LLP

(57) ABSTRACT

The present invention provides a human apoptosis regulator protein (Aven) and polynucleotides which identify and encode Aven. The invention also provides genetically engineered expression vectors and host cells comprising the nucleic acid sequences encoding Aven, and a method for producing Aven. The invention also provides for agonists, antibodies, or antagonists specifically binding Aven, and their use, in the prevention and treatment of diseases associated with expression of Aven. Additionally, the invention provides for the use of antisense molecules to polynucleotides encoding Aven for the treatment of diseases associated with the expression of Aven. The invention also provides diagnostic assays which utilize the polynucleotide, or fragments or the complement thereof, and antibodies specifically binding Aven.

8 Claims, 24 Drawing Sheets

| | | | | |
|---|---|---|---|---|
| MQAERGARGG | RGRRPGRGRP | GGDRHSERPG | AAAAVARGGG | 40 |
| GGGGGDGGGR | RGRGRGRGFR | GARGGRGGGG | APRGRRREPG* | 80 |
| GWGAGASAPV | EDDSDAETYG | EENDEQGNYS | KRKIVSNWDR | 120 |
| YQDIEKEVNN | ESGESQRGTD | FSVLLSSAGD | SFSQFRFAEE | 160 |
| KEWDSEASCP | KQNSAFYVDS | ELLVRALQEL | PLCLRLNVAA | 200 |
| ELVQGTVPLE | VPQVKPKRTD | DGKGLGMQLK | GPLGPGGRGP | 240 |
| IFELKSVAAG | CPVLLGKDNP | SPGPSRDSQK | PTSPLQSAGD | 280 |
| HLEEELDLLL | NLDAPIKEGD | NILPDQTSQD | LKSKEDGEVV | 320 |
| QEEEVCAKPS | VTEEKNMEPE | QPSTSKNVTE | EELEDWLDSM | 360 |
| IS | | | | 362 |

OTHER PUBLICATIONS

Moriishi et al.; "Bcl–2 family members do not inhibit apoptosis by binding the caspase activator Apaf–1", Proc. Natl. Acad. Sci. USA, vol. 96, Aug. 1999, pp. 9683–9688.

Qin et al.; "Structural basis of procaspase–9 recruitment by the apoptotic protease–activating factor 1"; Nature, vol. 399, Jun. 10, 1999, pp. 549–557.

Heiden et al.; "Bcl–$x_L$ Regulates the Membrane Potential and Volume Homeostasis of Mitochondria", Cell, vol. 91, Nov. 28, 1997, pp. 627–637.

Hu et al.; "Bcl–$X_L$ interacts with Apaf–1 and inhibits Apaf–1–dependent caspase–9 activation", Proc. Natl. Acad. Sci. USA, vol. 95, Apr. 1998, pp. 4386–4391.

Chinnaiyan et al.; "Interaction of CED–4 with CED–3 and CED–9: A Molecular Framework for Cell Death", Science, vol. 275, Feb. 21, 1997, pp. 1122–1126.

Kluck et al.; "The Release of Cytochrome c from Mitochondria: A Primary Site for Bcl–2 Regulation of Apoptosis" Science, vol. 275, Feb. 21, 1997, pp. 1132–1136.

Black et al.; "Injected cytochrome c induces apoptosis", Nature, vol. 391, Jan. 29, 1998, pp. 449–450.

Rosse et al.; "Bcl–2 prolongs cell survival after Bax–induced release of cytochrome c"; Nature, vol. 391, Jan. 29, 1998, pp. 496–499.

Susin et al.; "Molecular characterization of mitochondrial apoptosis–inducing factor", Nature, vol. 397, Feb. 4, 1999, pp. 441–446.

Shimizu et al.; "Bcl–2 family proteins regulate the release of apoptogenic cytochrome c by the mitochondrial channel VDAC", Nature, vol. 399, Jun. 3, 1999, pp. 483–487.

Pan et al.; "Caspase–9, Bcl–$X_L$, and Apaf–1 Form a Ternary Complex*"; The Journal of Biological Chemistry, vol. 273, No., 10, Issue of Mar. 6, 1998, pp. 5841–5845.

Metzstein et al.; "Genetics of programmed cell death in C. elegans: past, present and future", Elsevier Science Ltd., TIG Oct. 1998, vol. 14, No. 10, pp. 410–416.

Adams et al.; "The Bcl–2 Protein Family: Arbiters of Cell Survival", Science, vol. 281, Aug. 28, 1998, pp. 1322–1326.

Cain et al.; "Apaf–1 Oligomerizes into Biologically Active ~700–kDa and Inactive ~1.4–MDa apoptosome Complexes*", The Journal of Biological Chemistry, vol. 275, No. 9, Issue of Mar. 3, 2000, pp. 6067–6070.

Hausmann et al.; "Pro–apoptotic Apoptosis Protease–activating Factor 1 (Apaf–1) Has a Cytoplasmic Location Distinct from Bcl–2 or Bcl–$X_L$"; The Journal of Cell Biology, vol. 149, No. 3, May 1, 2000, pp. 623–633.

Yang et al.; "Prevention of apoptosis by Bcl–2: Release of Cytochrome c from Mitochondria Blocked", Science, vol. 275, Feb. 21, 1997, pp. 1129–1132.

Yang et al.; "Autoproteolytic Activation of Pro–Caspases by Oligomerization", Molecular Cell, vol. 1, Jan. 1998, pp. 319–325.

Cain et al.; "Caspase Activation Involves the formation of the Aposome, a Large (~700 kDa) Caspase–activating Complex*", The Journal of Biological Chemistry, vol. 274, No. 32, Issue of Aug. 6, 1999, pp. 22686–22692.

Li et al.; "Cytochrome c and dATP–Dependent Formation of Apaf–1/Caspase–9 Complex Initiates an Apoptotic Protease Cascade", Cell, vol. 91, Nov. 14, 1997, pp. 479–489.

Rodriguez et al.; "Caspase–9 and APAF–1 form an active holoenzyme", Genes & Development 13, 1999, pp. 3179–3184.

Zou et al.; "Apaf–1, a Human Protein Homologous to C. elegans CED–4, Participates in Cytochrome c–Dependent Activation of Caspase–3", Cell, vol. 90, Aug. 8, 1997, pp. 405–413.

Saleh et al.; "Cytochrome c and dATP–mediated Oligomerization of Apaf–1 Is a Prerequisite for Procaspase–9 Activation*", The Journal of biological Chemistry, vol. 274, No. 25, Issue of Jun. 18, 1999, pp. 17941–17945.

Zou et al.; "An APAF–1•Cytochrome c Multimeric Complex Is a Functional Apoptosome That Activates Procaspase–9*", The Journal of Biological Chemistry, vol. 274, Issue of Apr. 23, 1999, pp. 11549–11556.

Hu et al.; "Role of cytochrome c and dATP/ATP hydrolysis in Apaf–1–mediated caspase–9 activation and apoptosis", The EMBO Journal, vol. 18, No. 13, 1999, pp. 3586–3595.

Results of a Jun. 29, 2000 BLAST (Basic Local Alignment Search Tool) search of the Aven coding nucleotide sequence (1089 nucleotides) in the GenBank Human EST database (http://www.ncbi.nlm.nih.gov/BLAST/).

Results of a Jun. 29, 2000 BLAST (Basic Local Alignment Search Tool) search of the Aven nucleotide coding sequences (1089 nucleotides) in the GenBank Mouse EST database (http://www.ncbi.nlm.nih.gov/BLAST/).

WO 92/05256 A1 (Genetics Institute, Inc.; The Wistar Institute) Apr. 2, 1992 (Feb. 4, 1992).

Notification of Transmittal of the International Search Report dated Aug. 9, 2000.

Rooney et al. ,pp. 285–307 in Clinical Diagnosis & Management by Laboratory Methods, ed., Henry, J.B., 18 ed., W.B. Saunders Company, Philadelphia, 1991.*

Benet et al., pp. 3–32, in The Pharmacological Basis of Therapeutics, 8th ed., McGraw–Hill, Inc. New York, 1990.*

Rice et al., Advances in Pharmacology, 33:289–438, 1995.*

Gura, T., Science, 278:1041–1042, Nov. 1997.*

Robertson et al., Critical Reviews in Toxicology 30/5:609–627, 2000.*

* cited by examiner

```
MQAERGARGG  RGRRPGRGRP  GGDRHSERPG  AAAAVARGGG      40
                                            *
GGGGGDGGGR  RGRGRGRGFR  GARGGRGGGG  APRGRRREPG      80
GWGAGASAPV  EDDSDAETYG  EENDEQGNYS  KRKIVSNWDR     120
YQDIEKEVNN  ESGESQRGTD  FSVLLSSAGD  SFSQFRFAEE     160
KEWDSEASCP  KQNSAFYVDS  ELLVRALQEL  PLCLRLNVAA     200
ELVQGTVPLE  VPQVKPKRTD  DGKGLGMQLK  GPLGPGGRGP     240
IFELKSVAAG  CPVLLGKDNP  SPGPSRDSQK  PTSPLQSAGD     280
HLEEELDLLL  NLDAPIKEGD  NILPDQTSQD  LKSKEDGEVV     320
QEEEVCAKPS  VTEEKNMEPE  QPSTSKNVTE  EELEDWLDSM     360
IS                                                 362
```

FIG. 1

```
                10         20         30         40         50         60
         GGGCGTCTCCGCAGCTCGGCTCCCGCGCGCTCAGCACCACCAGCGGCGCCAGATGCAGGC
         CCCGCAGAGGCGTCGAGCCGAGGGCGCGCGAGTCGTGGTGGTCGCCGCGGTCTACGTCCG
                                                               M  Q  A>

70         80         90        100        110        120
         GGAGCGAGGAGCTCGGGGAGGCCGTGGGCGGCGGCCAGGCCGCGGCCCGGCCTGGCGGAGA
         CCTCGCTCCTCGAGCCCCTCCGGCACCCGCCGCCGGTCCGGCGCCGGCCGGACCGCCTCT
          E  R  G  A  R  G  G  R  G  R  R  P  G  R  G  R  P  G  G  D>

130        140        150        160        170        180
         TCGCCACAGCGAGCGGCCCGGAGCCGCAGCGGCGGTAGCCAGAGGCGGCGGCGGAGGCGG
         AGCGGTGTCGCTCGCCGGGCCTCGGCGTCGCCGCCATCGGTCTCCGCCGCCGCCTCCGCC
          R  H  S  E  R  P  G  A  A  A  A  V  A  R  G  G  G  G  G>

190        200        210        220        230        240
         CGGCGGGGACGGAGGCGGACGCCGGGGCCGTGGCCGTGGCCGGGGCTTCCGCGGCGCTCG
         GCCGCCCCTGCCTCCGCCTGCGGCCCCGGCACCGGCACCGGCCCCGAAGGCGCCGCGAGC
          G  G  D  G  G  R  R  G  R  G  R  G  R  G  F  R  G  A  R>

250        260        270        280        290        300
         CGGAGGCCGAGGAGGAGGAGGCGCCCCGCGAGGCAGCCGCCGGGAGCCGGGAGGCTGGGG
         GCCTCCGGCTCCTCCTCCTCCGCGGGGCGCTCCGTCGGCGGCCCTCGGCCCTCCGACCCC
          G  R  G  G  G  A  P  R  G  S  R  R  E  P  G  G  W  G>

310        320        330        340        350        360
         CGCAGGGGCCAGCGCGCCGGTTGAAGATGACAGCGATGCAGAGACCTATGGAGAAGAGAA
         GCGTCCCCGGTCGCGCGGCCAACTTCTACTGTCGCTACGTCTCTGGATACCTCTTCTCTT
          A  G  A  S  A  P  V  E  D  D  S  D  A  E  T  Y  G  E  E  N>

370        380        390        400        410        420
         TGATGAACAGGGAAATTATTCTAAAAGAAAGATTGTCTCTAACTGGGATCGATATCAAGA
         ACTACTTGTCCCTTTAATAAGATTTTCTTTCTAACAGAGATTGACCCTAGCTATAGTTCT
          D  E  Q  G  N  Y  S  K  R  K  I  V  S  N  W  D  R  Y  Q  D>

430        440        450        460        470        480
         TATTGAAAAAGAGGTCAATAATGAAAGTGGAGAGTCACAGAGGGGAACAGATTTCAGTGT
         ATAACTTTTTCTCCAGTTATTACTTTCACCTCTCAGTGTCTCCCCTTGTCTAAAGTCACA
          I  E  K  E  V  N  N  E  S  G  E  S  Q  R  G  T  D  F  S  V>

490        500        510        520        530        540
         CCTCCTTAGCTCTGCAGGGGACTCATTCTCACAGTTCCGGTTTGCTGAGGAGAAAGAATG
         GGAGGAATCGAGACGTCCCCTGAGTAAGAGTGTCAAGGCCAAACGACTCCTCTTTCTTAC
          L  L  S  S  A  G  D  S  F  S  Q  F  R  F  A  E  E  K  E  W>
```

FIG.2A

```
         550       560       570       580       590       600
GGATAGTGAAGCTTCTTGTCCAAAACAGAATTCAGCATTTTATGTGGATAGTGAGTTATT
CCTATCACTTCGAAGAACAGGTTTTGTCTTAAGTCGTAAAATACACCTATCACTCAATAA
  D  S  E  A  S  C  P  K  Q  N  S  A  F  Y  V  D  S  E  L  L>

610       620       630       640       650       660
GGTTCGAGCCCTTCAAGAGCTGCCTCTCTGCCTCCGACTCAACGTTGCTGCCGAACTGGT
CCAAGCTCGGGAAGTTCTCGACGGAGAGACGGAGGCTGAGTTGCAACGACGGCTTGACCA
  V  R  A  L  Q  E  L  P  L  C  L  R  L  N  V  A  A  E  L  V>

670       680       690       700       710       720
CCAGGGTACAGTTCCTTTAGAGGTTCCTCAGGTGAAACCAAAGAGAACTGATGATGGCAA
GGTCCCATGTCAAGGAAATCTCCAAGGAGTCCACTTTGGTTTCTCTTGACTACTACCGTT
  Q  G  T  V  P  L  E  V  P  Q  V  K  P  K  R  T  D  D  G  K>

730       740       750       760       770       780
GGGATTAGGGATGCAGTTAAAGGGGCCCTTGGGGCCTGGAGGAAGGGGGCCCATCTTTGA
CCCTAATCCCTACGTCAATTTCCCCGGGAACCCCGGACCTCCTTCCCCCGGGTAGAAACT
  G  L  G  M  Q  L  K  G  P  L  G  P  G  G  R  G  P  I  P  E>

790       800       810       820       830       840
GCTGAAATCTGTGGCTGCTGGCTGCCCTGTGTTGCTGGGCAAAGACAACCCAAGCCCGGG
CGACTTTAGACACCGACGACCGACGGGACACAACGACCCGTTTCTGTTGGGTTCGGGCCC
  L  K  S  V  A  A  G  C  P  V  L  L  G  K  D  N  P  S  P  G>

850       860       870       880       890       900
TCCTTCAAGGGATTCTCAGAAACCCACTTCCCCACTGCAGTCAGCAGGAGACCATTTGGA
AGGAAGTTCCCTAAGAGTCTTTGGGTGAAGGGGTGACGTCAGTCGTCCTCTGGTAAACCT
  P  S  R  D  S  Q  K  P  T  S  P  L  Q  S  A  G  D  H  L  E>

910       920       930       940       950       960
AGAAGAACTAGATCTGTTGCTTAATTTAGATGCACCTATAAAAGAGGGAGATAACATCTT
TCTTCTTGATCTAGACAACGAATTAAATCTACGTGGATATTTTCTCCCTCTATTGTAGAA
  E  E  L  D  L  L  N  L  D  A  P  I  K  E  G  D  N  I  L>

970       980       990      1000      1010      1020
ACCAGATCAGACGTCTCAGGACCTGAAATCCAAGGAAGATGGGGAGGTGGTCCAAGAGGA
TGGTCTAGTCTGCAGAGTCCTGGACTTTAGGTTCCTTCTACCCCTCCACCAGGTTCTCCT
  P  D  Q  T  S  Q  D  L  K  S  K  E  D  G  E  V  V  Q  E>

1030      1040      1050      1060      1070      1080
AGAAGTTTGTGCAAAACCATCTGTGACTGAAGAAAAAAACATGGAACCTGAGCAACCAAG
TCTTCAAACACGTTTTGGTAGACACTGACTTCTTTTTTTGTACCTTGGACTCGTTGGTTC
  E  V  C  A  K  P  S  V  T  E  E  K  N  M  E  P  E  Q  P  S>
```

FIG.2B

```
          1090      1100      1110      1120      1130      1140
TACCTCCAAAAATGTTACCGAGGAAGAGCTGGAAGACTGGTTGGACAGCATGATTTCCTA
ATGGAGGTTTTTACAATGGCTCCTTCTCGACCTTCTGACCAACCTGTCGTACTAAAGGAT
    T  S  K  N  V  T  E  E  E  L  E  D  W  L  D  S  M  I  S  *>
          1150      1160      1170      1180      1190      1200
AAAAGGGGGAAAAAAGTGCCTGAAGCAAATCTTGGTTGCCTTCTAACGGCAGGTGGGCAT
TTTTCCCCCTTTTTTCACGGACTTCGTTTAGAACCAACGGAAGATTGCCGTCCACCCGTA
          1210      1220      1230      1240      1250      1260
AAGGCTGTCCTTCAGGACCAGCCAGTTTACAAGCATGTCTCAAGCTAGTGTGTTCCATTA
TTCCGACAGGAAGTCCTGGTCGGTCAAATGTTCGTACAGAGTTCGATCACACAAGGTAAT
          1270      1280      1290      1300      1310      1320
TGCTCACAGCAGTAAATGCCTACCTCTGTGTTTGACATCTGAAAGAATACATTGAAGCAG
ACGAGTGTCGTCATTTACGGATGGAGACACAAACTGTAGACTTTCTTATGTAACTTCGTC
          1330      1340      1350      1360      1370      1380
CTTGTTGCATTTGTTTTTCTGGCTTAGTAATCTAATAGATTTCCTTAAGGGCAGGAGATA
GAACAACGTAAACAAAAAGACCGAATCATTAGATTATCTAAAGGAATTCCCGTCCTCTAT
          1390      1400      1410      1420      1430      1440
GACTCTGGCCCTTGTTTCTAGCCTCCTTCCTTGCAGTGTTTACAACATAGCCAGTGTTTA
CTGAGACCGGGAACAAAGATCGGAGGAAGGAACGTCACAAATGTTGTATCGGTCACAAAT
          1450      1460      1470      1480      1490      1500
CAGCATAGCAGATGCTGCTGCTGGTTAAGAGAATAGATGCAAACAAGGCATGCATTTGGC
GTCGTATCGTCTACGACGACGACCAATTCTCTTATCTACGTTTGTTCCGTACGTAAACCG
          1510      1520      1530      1540      1550      1560
CAAAATAAACAAATGCTGGTCTGTCCAAAAAANNAAAAAAAAAAAAAAAAGGCCTTCGTGG
GTTTTATTTGTTTACGACCAGACAGGTTTTTTNNTTTTTTTTTTTTTTTTCCGGAAGCACC
CCTCGA
GGAGCT
```

FIG.2C

Spleen
Thymus
Prostate
Testis
Ovary
Small intestine
Colon
Peripheral blood leukocyte Aven

|  | Y2H | CoIP |
|---|---|---|
| Bcl-XL | + | + |
| Bcl-2 | + | + |
| Ksbcl-2 | + | + |
| Bak | − | NT |
| Bax | − | NT |
| Bcl-XL mt1 | + | + |
| Bcl-XL mt7 | − | − |
| ΔN61 Bcl-XL | NT | − |
| Δloop Bcl-XL | NT | + |

FIG.6

Lysate　　　　　　　　　　　　　　　　　　　　Blotted with
Bcl-x$_L$ →　　　　　　　　　< 
　　　　　　　　　　　　　　　　　αBcl-x$_L$
ΔN61 Bcl-x$_L$ →
< αBcl-x$_L$ (2A1) detects both tranfected and endogenous Bcl-xL
Co-IP with αBif-1b
HA-Bif-1 →　　　　　　　　　αHA
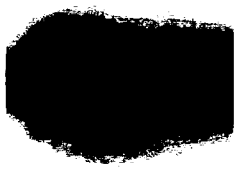
Bcl-x$_L$ →　　　　　　　　　αBcl-x$_L$
FIG. 7A

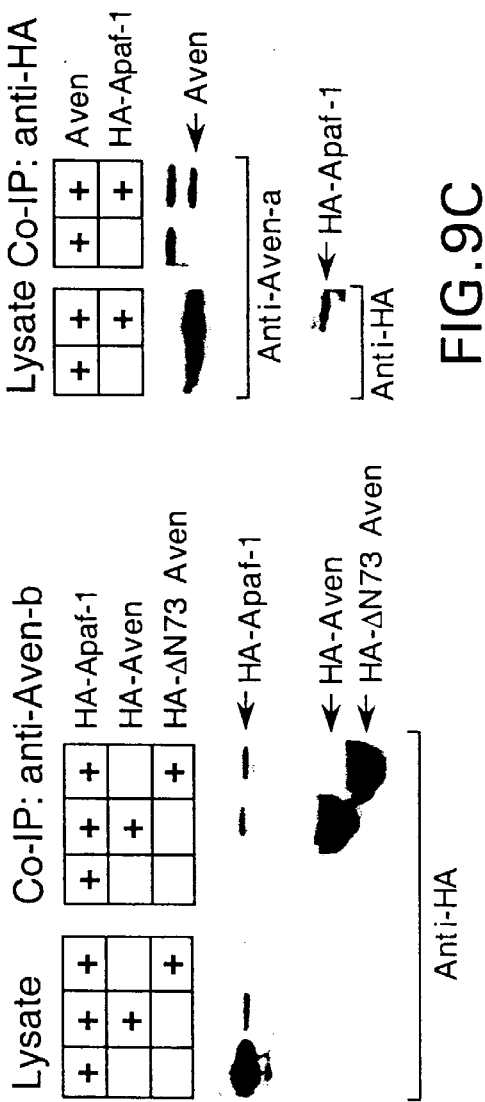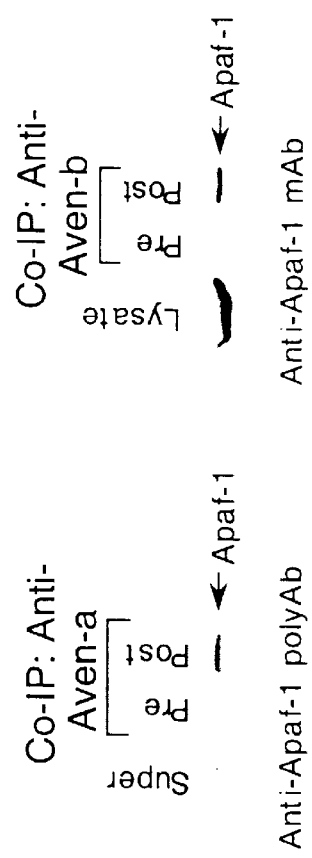

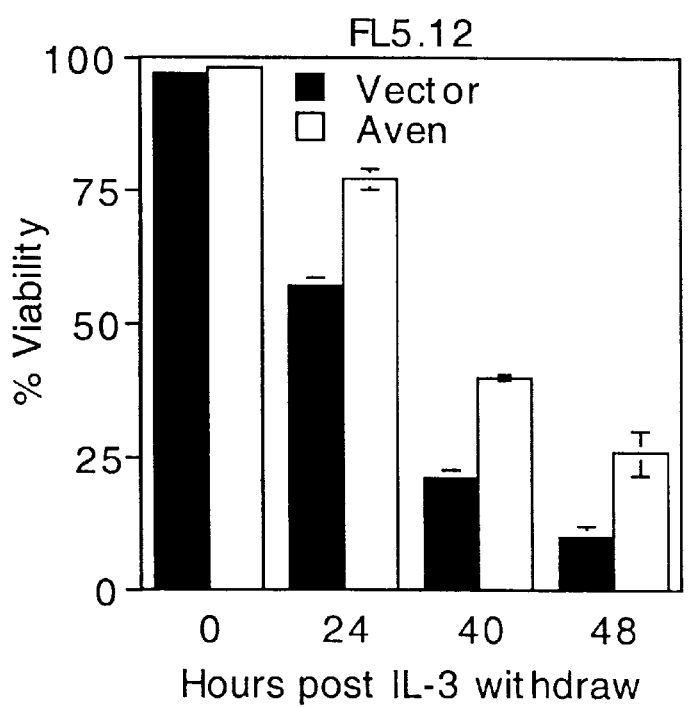
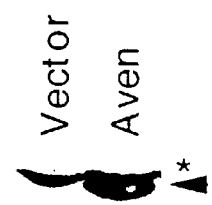
FIG.12A
FIG.12B

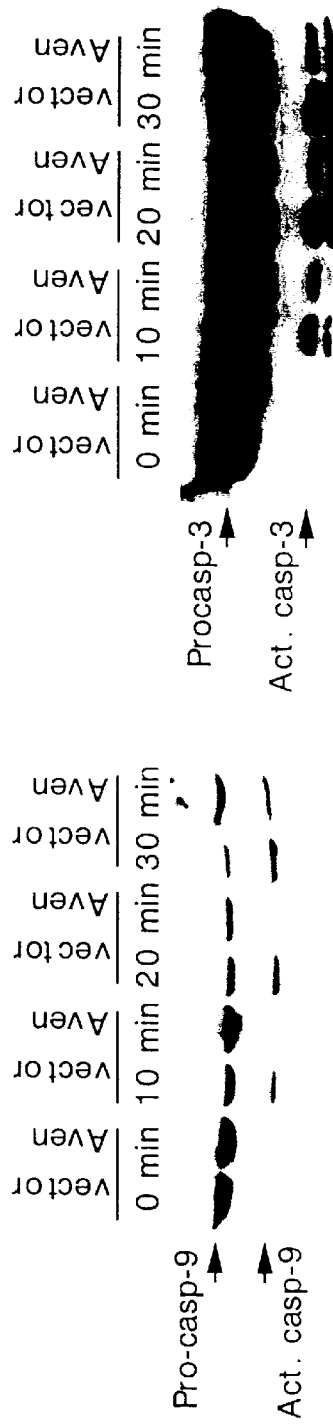
FIG. 15A
FIG. 15B
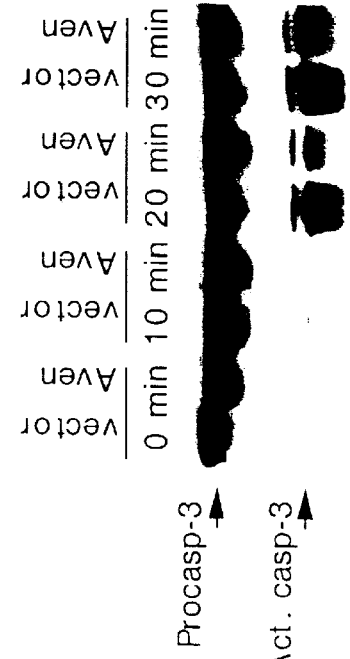
FIG. 15D
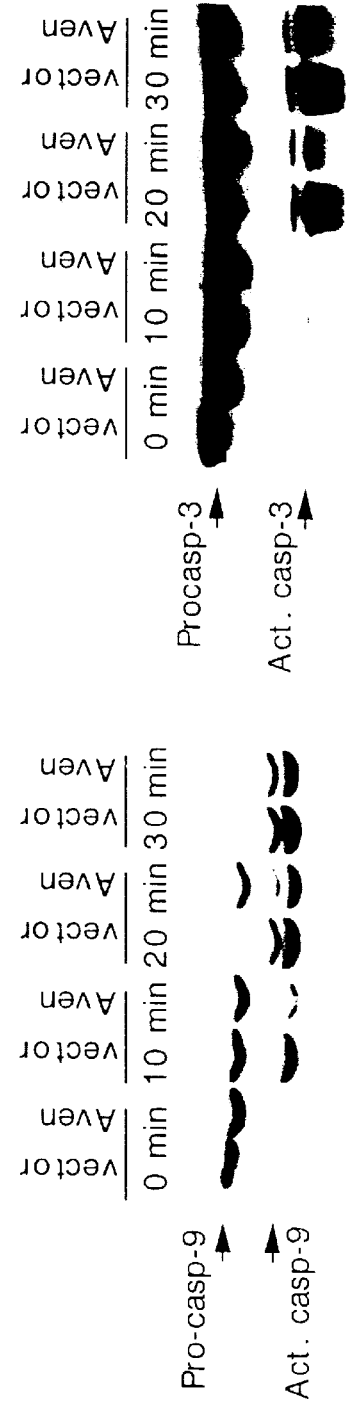
FIG. 15C

INHIBITOR OF PROGRAMMED CELL DEATH

This application claims priority from U.S. provisional application, Ser. No. 60/122,104 filed Feb. 26, 1999, the entirety of which is incorporated herein by reference.

Government interest: This invention was made with government support under Grant No. NIH NS34175 awarded by the National Institutes of Health. The government has certain rights in the invention.

FIELD OF THE INVENTION

This invention relates to nucleic acid and amino acid sequences of a novel inhibitor of programmed cell death, the protein Aven, and to the use of these sequences in the diagnosis, prevention, and treatment of diseases associated with decreased or increased apoptosis.

BACKGROUND OF THE INVENTION

Normal development, growth, and homeostasis in multicellular organisms require a careful balance between the production and destruction of cells in tissues throughout the body. Cell division is a carefully coordinated process with numerous checkpoints and control mechanisms. These mechanisms are designed to regulate DNA replication and to prevent inappropriate or excessive proliferation. In contrast, apoptosis is the genetically controlled process by which unneeded or damaged cells can be eliminated without causing the tissue destruction and inflammatory responses that are often associated with acute injury and necrosis.

The term "apoptosis" was first used to describe the morphological changes that characterize cells undergoing programmed cell death. Apoptotic cells have a shrunken appearance with an altered membrane lipid content and highly condensed nuclei. Apoptotic cells are rapidly phagocytosed by neighboring cells or macrophages without leaking their potentially damaging contents into the surrounding tissue or triggering an inflammatory response.

The processes and mechanisms regulating apoptosis are highly conserved throughout the phylogenetic tree, and much of our current knowledge about apoptosis is derived from studies of the nematode *Caenorhabditis elegans* and the fruit fly *Drosophila melanogaster*. Aberrations in apoptosis regulation have recently been recognized as significant factors in the pathogenesis of human disease. For example, inappropriate cell survival can cause or contribute to many diseases such as cancer, autoimmune diseases, and inflammatory diseases. In contrast, increased apoptosis can cause immunodeficiency diseases such as AIDS, neurodegenerative disorders, and myelodysplastic syndromes.

A variety of ligands and their cellular receptors, enzymes, tumor suppressors, viral gene products, pharmacological agents, and inorganic ions have important positive or negative roles in regulating and implementing the apoptotic destruction of a cell. Although some specific components of the apoptotic pathway have been identified and characterized, many interactions between the proteins involved are undefined, leaving major aspects of the pathway unknown. Despite the identification of genes necessary for cell death and the ability to regulate apoptosis by known genes, the essential biochemical events in apoptotic death remain largely unknown.

The consistency of the morphologic and biochemical patterns defined as apoptosis within different cell types and species, during normal development and as a response to external stimuli are consistent with a common cause of cellular mortality. The thesis is supported by the concept of an endogenous program responsible for cells death and the presence of gene products which are positive and negative regulators of apoptosis. The best studied negative regulator of apoptosis is the Bcl-2 proto-oncogene product. It provides the strongest evidence for a sharedmammalian pathway of death by its ability to block a wide variety of cell death models.

The Bcl-2 proto-oncogene is rather unique among cellular genes in its ability to block apoptotic deaths in multiple contexts. Overexpression of Bcl-2 in transgenic models leads to accumulation of cells due to evasion of normal cell death mechanisms. Induction of apoptosis by diverse stimuli, such as radiation, hyperthermia, growth factor withdrawal, glucocorticoids and multiple classes of chemotherapeutic agents is inhibited by Bcl-2 in vitro models. These effects are proportional to the level of Bcl-2 expression. Additionally, the endogenous pattern of Bcl-2 expression is indicative of a role in the regulation of cell survival in vivo. The Bcl-2 protein seems likely to function as an antagonist of a central mechanism operative in cell death.

The protein encoded by the Bcl-2 proto-oncogene has been reported to be capable of inhibiting apoptosis in many hematopoietic cell systems. The proto-oncogene Bcl-2 was isolated and characterized as a result of its frequent translocation adjacent to the immunoglobulin heavy chain enhancer in the t(14;18) chromosome translocation present in more than 80% of human follicular lymphomas. These neoplasias are characterized by an accumulation of mature resting B cells presumed to result from a block of apoptosis which would normally cause turnover of these cells. Transgenic mice expressing Bcl-2 under the control of the Eμ enhancer similarly develop follicular lymphomas.

The Bcl-2 protein is a 26 kDa membrane-associated cytoplasmic protein. Unlike many other proto-onocogene products, the Bcl-2 protein apparently functions, at least in part, by enhancing the survival of hematopoietic cells of T and B origins rather than by directly promoting proliferation of these cell types. The capacity of Bcl-2 to enhance cell survival is related to its ability to inhibit apoptosis initiated by several factors, such as cytokine deprivation, radiation exposure, glucocorticoid treatment, and administration of anti-CD-3 antibody. Upregulation of Bcl-2 expression also inhibits apoptosis of EBV-infected B-cell lines. The expression of Bcl-2 has also been shown to block apoptosis resulting from expression of the positive cell growth regulatory proto-oncogene, c-myc, in the absence of serum or growth factors.

Within vertebrates, Bcl-2 is the best understood gene in a cell death pathway and functions as a cell death repressor. Other proteins which interact with and/or are structurally related to the Bcl-2 gene product have also been identified, such as, for example, Bcl-$x_L$ and Bcl-$x_S$. The family of Bcl-2 related proteins also includes the nematode protein CED-9 and two DNA virus proteins, LMW5-HL and BHRF-1 of the Epstein Barr Virus. Thus, a family of Bcl-2 like genes exists and evidence indicates that they participate in regulating cell death.

The family of Bcl-2 related proteins has been noted to have homology that is principally, but not exclusively, clustered within two conserved regions entitled Bcl-homology 1 and 2 (BH1 and BH2). This includes Bax, Bcl-$X_L$, Mcl-1 and Al, and several open reading frames in DNA viruses including BHRF-1 of Epstein-Barr virus and LMW5-HL of African swine fever virus.

It has been discovered that Bcl-2 also associates in vivo with a 21 kDa protein partner called Bax. Bax shows extensive amino acid homology with Bcl-2 and forms homodimers with itself and heterodimers with Bcl-2 in vivo. Bax is encoded by 6 exons and demonstrates a complex pattern of alternative RNA splicing that predicts a 21 KDa membrane ($\alpha$) and three forms ($\beta$, $\gamma$, and $\omega$)) of cytosolic protein. Bcl-2 and Bax have biochemical functions that are yet to be delineated but may also modulate cell death/survival through heterodimerization. When Bax predominates and a substantial percentage of Bax is present as homomultimers (e.g., homodimers) and/or free (unbound) Bax monomer or other activated form or complex, programmed cell death is accelerated and the death repressor activity of Bcl-2 is countered. In many cell types when in excess, Bax counters the ability of Bcl-2 to repress cell death. It was unexpected to find that Bax shares extensive homology with Bcl-2, especially within two highly conserved domains. These domains are also the most highly conserved regions of human, mouse, and chicken Bcl-2. These domains are also conserved in an open reading frame BHRF-1 within Epstein-Barr virus and Mcl-1, a gene recently isolated from a myeloid leukemia cell line following induction with phorbol ester.

The Bcl-x gene was identified by low-stringency hybridization using a Bcl-2 polynucleotide probe and encodes two proteins, Bcl-$x_L$ and Bcl-$x_S$, via alternative RNA splicing. The Bcl-$x_L$ cDNA encodes a polypeptide of 233 amino acids with similar domains to those of Bcl-2. The Bcl-$x_S$ cDNA encodes a polypeptide of 170 amino acids in which the region of highest homology to Bcl-2 has been deleted. When the ability of these two proteins to regulate apoptotic cell death was compared, it was found that Bcl-$x_L$ rendered cells resistant to apoptotic cell death induced by growth factor deprivation, whereas Bcl-$x_S$ could prevent overexpression of Bcl-2 from inducing resistance to apoptotic cell death. Thus, Bcl-$x_L$ can serve as an inhibitor of apoptotic cell death in a variety of cell lines, whereas Bcl-$x_S$ inhibits the ability of Bcl-2 to inhibit cell death and can make cells more susceptible to apoptotic cell death.

Many pathological conditions result, at least in part, from aberrant control of cell proliferation, differentiation and/or apoptosis. For example, neoplasia is characterized by a clonally derived cell population which has a diminished capacity for responding to normal cell proliferation control signals. Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes.

The precise molecular pathways and secondary changes leading to malignant transformation for many cell types are not clear. However, the characteristic translocation of the apoptosis-associated Bcl-2 gene to the immunoglobulin heavy chain locus t(14;18) in more than 80 percent of human follicular B cell lymphomas and 20 percent of diffuse lymphomas and the neoplastic follicular lymphoproliferation present in transgenic mice expressing high levels of Bcl-2 indicates that the Bcl-2 gene likely is causally involved in neoplastic diseases and other pathological conditions resulting from abnormal apoptosis, cell proliferation, and differentiation. Thus, it is desirable to identify agents which can modify the activity(ies) of Bcl-2-related proteins so as to modulate apoptosis, cell proliferation, and differentiation for therapeutic or prophylactic benefit. Further, such agents can serve as commercial research reagents for control of apoptosis cell proliferation, and differentiation in experimental applications, and/or for controlled proliferation and differentiation of predetermined hematopoietic stem cell populations in vitro, in ex vivo therapy, or in vivo.

Despite progress in developing a more defined model of the molecular mechanisms underlying the transformed phenotype and neoplasia, few significant therapeutic methods applicable to treating cancer beyond conventional chemotherapy have resulted. Such Bcl-2-related protein modulating agents can provide novel chemotherapeutic agents for treatment of neoplasia, lymphoproliferative conditions, arthritis, inflammation, autoimmune diseases, and the like. The present invention fulfills these and other needs.

While identifying the Bcl-2 cell death pathway is significant, a way of regulating the Bcl-2 pathway has not been achieved. The ability to down-regulate the cell death repressing effect of Bcl-2 and/or up-regulate the cell death promoting activity of Bax would be advantageous in cancer therapy, in controlling hyperplasia such as benign prostatic hypertrophy (BPH) and eliminating self reactive clones in autoimmunity by favoring death effector molecules. Up-regulating the effect of Bcl-2 and favoring death repressor molecules would be beneficial in the treatment and diagnosis of immunodeficiency diseases, including AIDS, senescence, neurodegenerative disease, ischemic cell death, wound-healing, and the like.

The discovery of polynucleotides encoding a Bcl-$x_L$ interacting factor (Aven), and the molecules themselves, provides a means to investigate the regulation of programmed cell death and apoptosis. Discovery of molecules related to apoptosis regulator proteins satisfies a need in the art by providing new diagnostic or therapeutic compositions useful in the detection, prevention, and treatment of cancer, autoimmune diseases, lymphoproliferative disorders, atherosclerosis, AIDS, immunodeficiency diseases, ischemic injuries, neurodegenerative diseases, osteoporosis, myelodysplastic syndromes, toxin-induced diseases, and viral infections.

SUMMARY OF THE INVENTION

The present invention relates to the discovery that Bcl-$x_L$ interacts with a 55 kDa protein called Aven (also known as Bif-1 (Bcl-$x_L$, Interacting Factor-1)). It has been unexpectedly discovered that Aven interacts with apoptosis regulators including Bcl-2 family members such as Bcl-$x_L$, and Apaf-1 (a mammalian homologue of CED-4, and a facilitator of caspase-9 activation) independently. Aven enhances the anti-apoptotic function of Bcl-$x_L$, against caspase-1 induced apoptosis, as well as protecting cells from apoptosis induced by Apaf-1 and caspase-9. It has been demonstrated that Aven functions as an inhibitor of neuronal apoptosis in an animal model.

The present invention provides an isolated amino acid compound which comprises the amino acid sequence shown in FIG. 1, and functional equivalents thereof. Preferably the amino acid compound has the sequence shown in FIG. 1. The Aven amino acid sequence (SEQ ID NO: 2) shown in FIG. 1 has a Gly/Arg rich amino terminus, a central hydrophobic repeat with predicted alpha-helical structure, and a highly acidic carboxyl terminus. Examples of amino acid fragments which modulate the interaction with BCl-$x_L$ include amino acids 71–108 and amino acids 74–104 of FIG. 1. The Aven carboxy-terminus is required for the transcription activation properties of Aven. Deletion of the carboxyl terminus of Aven, from about amino acids 289–362, abolished this transcription activation function.

The invention also provides isolated nucleic acid compounds that comprise a nucleic acid sequence which encodes the presently provided amino acid compounds or parts thereof. Nucleic acid compounds which are DNA are preferred. The most preferred is the DNA compound having the sequence shown in FIG. 2 (SEQ ID NO: 1). Also provided are nucleic acid sequences that are homologous or complementary to any of the provided nucleic acid sequences, and sequences that hybridize to any of the provided nucleic acid sequence.

Expression vectors and host cells overexpressing the amino acid compounds or nucleic acid compounds of the present invention are also provided. The present invention also provides antibodies which bind specifically to Aven, and pharmaceutical compositions comprising substantially purified Aven. In addition, the invention provides agonists and antagonists of Aven. Also provided are stably transformed cell lines expressing the amino acid or nucleic acid compounds of the present invention, or the antibodies, agonists or antagonists of the present invention.

Additional advantages and features of the present invention will be apparent from the following detailed description, drawings and examples which illustrate preferred embodiments of the invention.

BRIEF DESCRIPTION OF THE DRAWINGS

FIG. 1 depicts the amino acid sequence of Aven (SEQ ID NO: 2).

FIG. 2 depicts the nucleotide sequence of the Aven (SEQ ID NO: 1) gene.

FIG. 6 depicts the interaction between Aven and various different Bcl-2 family members and BCI-$X_L$ mutants.

FIG. 7A is a co-immunoprecipitation analysis showing that Aven does not interact with pro-apoptotic proteins (ΔN 61 Bcl-$x_L$).

FIGS. 9A–E show the interaction between Aven and Apaf-1.

FIG. 10(c) also includes a Western blot of BHK cell lysates showing that comparable amounts of Apaf-1 and caspase-9 were expressed in either the presence or absence of Aven.

FIGS. 12A and 12B depict increased resistance to apoptosis induced by IL-3 withdrawl in pooled FL5.12 cells stably expressing Aven.

FIGS. 15A–D show that Aven inhibits activation of endogenous caspases.

DEFINITIONS

Figure 3:
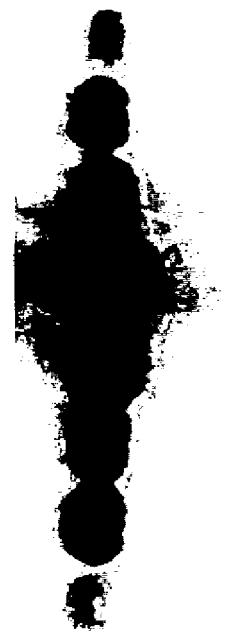
FIG. 3 is a multiple tissue Northern blot illustrating the expression of Aven in a wide variety of tissue.

The following abbreviations are used in this application: aa, amino acid(s); Ab, antibody(ies); bp, base pair(s); CoIP or Co-IP, co-immunoprecipitation; FISH, fluorescent in situ hybridization; kb, kilobase(s) or 1000 bp; LB, Luria-Bertoni media; mAb, monoclonal Ab; ORF, open reading frame; PCR, polymerase chain reaction; Tn, transposon(s); Y2H, yeast two-hybrid screen; ::, novel junction (fusion or insertion).

The term "agonist," as used herein, refers to a molecule which, when bound to Aven, or a Aven polypeptide causes a change in Aven which modulates the activity of Aven. Agonists may include proteins, nucleic acids, carbohydrates, or any other molecules which bind to Aven, or Aven polypeptides, either covalently or non-covalently.

"Alterations" in the polynucleotide of FIG. 2, as used herein, comprise any alteration in the sequence of polynucleotides encoding Aven including deletions, insertions, and point mutations that may be detected using hybridization assays. Included within this definition is the detection of alterations to the genomic DNA sequence which encodes Aven (e.g., by alterations in the pattern of restriction fragment length polymorphisms capable of hybridizing to FIG. 2), the inability of a selected fragment of FIG. 2 to hybridize to a sample of genomic DNA (e.g., using allele-specific oligonucleotide probes), and improper or unexpected hybridization, such as hybridization to a locus other than the normal chromosomal locus for the polynucleotide sequence encoding Aven (e.g., using FISH to metaphase chromosome spreads).

As used herein, the twenty conventional amino acids and their abbreviations follow conventional usage. One letter and three letter code designations for amino acids used herein are given in Table 1, below. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention.

Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

TABLE 1

Amino Acid Code Designations

| Amino Acid | Three letter code | One letter code |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Amplification," as used herein, refers to the production of additional copies of a nucleic acid sequence and is generally carried out using PCR technologies well known in the art. The terms "antagonist" or "inhibitor," as used herein, refer to a molecule which, when bound to Aven, or an Aven polypeptide blocks or modulates the biological or immunological activity of Aven. Antagonists and inhibitors may include proteins, nucleic acids, carbohydrates, or any other molecules which bind to Aven, or an Aven polypeptide either covalently or non-covalently.

As used herein, the term "antibody" refers to intact molecules as well as fragments thereof, such as Fab, F(ab')2, and Fv, which are capable of binding the epitopic determinant. Antibodies that bind Aven polypeptides can be prepared using intact polypeptides or fragments containing small peptides of interest as the immunizing antigen. The polypeptide or peptide used to immunize an animal can be derived from the translation of RNA or synthesized chemically, and can be conjugated to a carrier protein, if desired. Commonly used carriers that are chemically coupled to peptides include bovine serum albumin, keyhole limpet hemocyanine and thyroglobulin. The coupled peptide is then used to immunize the animal (e.g., a mouse, a rat, or a rabbit).

The term "antigenic determinant," as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

"Aven,", also termed "Bif-1", as used herein, refers to the amino acid sequences of substantially purified Aven obtained from any species, particularly mammalian, including bovine, ovine, porcine, murine, equine, drosophila, $C.$ $elegans$, yeast and preferably human, from any source whether natural, synthetic, semi-synthetic, or recombinant. The term "Aven polypeptide" is a generic term used to refer to native protein, fragments, or analogs of Aven, post-translational modifications, such as acetylation, carboxylation, glycosylation, phosphorylation, lipidation, ubiquitination or acylation of such proteins, fragments, or analogs, or such proteins, fragments or analogs fused to a second polypeptide sequence (e.g., an epitope tag, β-gal, or other fusion). Hence, native Aven, fragments of Aven, and analogs of Aven, as well as Aven fusion proteins are species of the Aven polypeptide genus.

"Bcl-2 family members" or "Bcl-2 family proteins" or the "Bcl-2 family" means apoptotic modulator proteins that contain one or more of the Bcl-2 hemology domains (BH-1, BH-2, BH-3, or BH-4) and, that upon expression in a cell, act to modulate or regulate the apoptotic process by either suppressing or promoting cell death. The term "anti-apoptotic protein" is used herein to refer to Bcl-2 family members which, upon expression in a cell, are typically associated with a suppression of programmed cell death (apoptosis). Examples of anti-apoptotic proteins are Bcl-2, Bcl-$x_L$, Bcl-w, Al, Afl-1, Nr13, CED-9, Elb (19 kDa), BHRF-1 and Mcl-1. The term "pro-apoptotic protein" is used herein to refer to Bcl-2 family members, which, upon expression in a cell, are typically associated with the induction of apoptosis. Bax, Bak, Bad, Bik, Bid, and Bcl-$x_S$ are examples of pro-apoptotic proteins. It should be understood, however, that delineation between pro-apoptotic and anti-apoptotic family members may be artificial because studies have shown that in certain circumstances a pro-apoptotic protein may act to suppress apoptosis, and an anti-apoptotic protein may act to promote apoptosis. The categorization of a particular protein as pro-or anti-apoptotic should therefore be regarded as a generalization about the protein activity based on current scientific understanding, and that it may be found to be inapplicable in a particular cellular circumstance.

The term "Bcl-2 polypeptide" is used herein as a generic term to refer to native protein, fragments, analogs, or fusions of Bcl-2, preferably human or murine Bcl-2. The term "Bcl-$x_L$ polypeptide" is used herein as a generic term to refer to native protein, fragments, analogs, or fusions of Bcl-$x_L$, preferably human or murine Bcl-$x_L$.

The term "biologically active," as used herein, refers to a protein having structural, regulatory, or biochemical functions of a naturally occurring molecule. Likewise, "immunologically active" refers to the capability of the natural, recombinant, or synthetic Aven, or any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "correlates with expression of a polynucleotide," as used herein, indicates that the detection of the presence of ribonucleic acid that is similar to FIG. 2 by Northern blot analysis is indicative of the presence of mRNA encoding Aven in a sample and thereby correlates with expression of the transcript from the polynucleotide encoding the protein.

A "deletion," as used herein, refers to a change in either amino acid or nucleotide sequence in which one or more amino acid or nucleotide residues, respectively, are absent. The term "derivative," as used herein, refers to the chemical modification of a nucleic acid encoding Aven or the encoded Aven. Illustrative of such modifications would be replacement of hydrogen by an alkyl, acyl, or amino group. A nucleic acid derivative would encode a polypeptide which retains essential biological characteristics of the natural molecule.

The term "homology," as used herein, refers to a degree of nucleotide or amino acid similarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or Northern blot, solution hybridization or the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of homology (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

"Host cells," as used herein, include, but are not limited to:

TABLE 2

Host Cell Lines

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| AV12-664 | Syrian Hamster | ATCC CRL 9595 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| 293 | Human Embryonal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |
| CHO-K1 | Chinese Hamster Ovary | ATCC CCL 61 |

The term "humanized antibody," as used herein, refers to antibody molecules in which amino acids have been replaced in the non-antigen binding regions in order to more closely resemble a human antibody, while still retaining the original binding ability.

The term "hybridization," as used herein, refers to any process by which a strand of nucleic acid binds with a complementary strand through base pairing. The term "hybridization complex," as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes,filters, chips, pins or glass slides to which cells have been fixed for in situ hybridization).

An "Iinsertion" or "addition," as used herein, refers to a change in an amino acid or nucleotide sequence resulting in the addition of one or more amino acid or nucleotide residues, respectively, as compared to the naturally occurring molecule.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I) fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

The term "mimetic," as used herein, refers to a molecule, the structure of which is developed from knowledge of the structure of Aven or portions thereof and, as such, is able to effect some or all of the actions of apoptosis regulator-like molecules. The term "modulate," as used herein, refers to a change or an alteration in the biological activity of Aven. Modulation may be an increase or a decrease in protein activity, a change in binding characteristics, or any other change in the biological, functional or immunological properties of Aven.

"Nucleic acid sequence," as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

"Peptide nucleic acid," as used herein, refers to a molecule which comprises an oligomer to which an amino acid residue, such as lysine, and an amino group have been added. These small molecules, also designated anti-gene agents, stop transcript elongation by binding to their complementary strand of nucleic acid. The term "portion," as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of FIG. 1" encompasses the fill-length human Aven and fragments thereof.

The term "sample," as used herein, is used in its broadest sense. A biological sample suspected of containing nucleic acid encoding Aven or fragments thereof may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support), an extract from cells or a tissue, and the like.

The terms "specific binding" or "specifically binding," as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in lo general. For example, if an antibody is specific for epitope "A", the presence of a protein containing epitope A (or free, unlabeled A) in a reaction containing labeled "A" and the antibody will reduce the amount of labeled A bound to the antibody.

The term "stringent conditions," as used herein, is the "stringency" which occurs within a range from about $T_m$–5° C. (5° C. below the melting temperature ($T_m$) of the probe) to about 20° C. to 25° C. below $T_m$. As will be understood by those of skill in the art, the stringency of hybridization may be altered in order to identify or detect identical or related polynucleotide sequences.

The term "substantially purified," as used herein, refers to nucleic or amino acid sequences that are removed from their natural environment, isolated or separated, and are at least 60% free, preferably 75% free, and most preferably 90% free from other components with which they are naturally associated. A "substitution," as used herein, refers to the replacement of one or more amino acids or nucleotides by different amino acids or nucleotides, respectively.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stable transformed cells in which the inserted DNA is capable of replication either as an autonomously replicating plasmid or as part of the host chromosome. They also include cells which transiently express the inserted DNA or RNA for limited periods of time.

A "variant" of Aven, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR™ software (sequence analysis). A preferred Aven variant is one having at least 80%, and more preferably 90%, amino acid sequence similarity to the Aven amino acid sequence (FIG. 1). A most preferred Aven variant is one having at least 95% amino acid sequence similarity to FIG. 1.

DETAILED DESCRIPTION OF PREFERRED EMBODIMENTS

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural, biological, and chemical changes may be made without departing from the spirit and scope of the present invention.

It must be noted that as used herein and in the appended claims, the singular forms "a," "an," and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined othenvise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference. Nothing herein is to be construed as an admission that the invention is not entitled to antedate such disclosure by virtue of prior invention.

The present invention concerns the novel human apoptosis regulator protein Aven in an isolated, purified, and/or recombinant form, and the use of Aven, Aven polypeptides, nucleic acids encoding Aven, and the use of these compositions for the diagnosis, prevention, or treatment of cancer, autoimmune diseases, lymphoproliferative disorders, atherosclerosis, AIDS, immunodeficiency diseases, ischemic injuries, neurodegenerative diseases, osteoporosis, myelodysplastic syndromes, toxin-induced diseases, viral infections, and other diseases related to apoptosis. Aven, which has been shown by the inventors to interact with anti-apoptotic Bcl-2 family members including Bcl-$x_L$, and with Apaf-1, has been isolated, characterized, and named by the present inventors.

Nucleic acids encoding the human Aven of the present invention were first identified in a yeast two-hybrid screen for proteins that interact with Bcl-$x_L$. Six different clones were isolated, one of which has been named Bcl-$x_L$ Interacting Factor-1 (Aven), the amino acid sequence (SEQ ID NO: 2) of which is shown in FIG. 1. Referring now to the drawings, the amino acid sequence of Aven (SEQ ID NO: 2) is shown in FIG. 1. As can be seen, Aven comprises 362 amino acids and has a Gly/Arg rich amino terminus and a highly acidic carboxyl terminus. The predicted size of Aven was approximately 40 kDa, but Aven produced from transfection and in vitro transcription and translation consistently migrates with an apparent MW of 55 kDa, suggesting that Aven may be modified post-translationally. On the other hand, the altered migration may be due to folding and sequence effects, and not to post-translational modification. The amino acid sequence of Aven has no known homologies to previously known proteins.

The DNA sequence encoding the Aven (SEQ ID NO: 1) of the present invention, which comprises 1566 base pairs, is shown in FIG. 2. Both strands are shown, with the 5' end on the left and the 3' end on the right. The start codon (ATG) (bp 53–55) and stop codon (TAA) (bp 1139–41) are underlined. Several dozen base pairs upstream of the start codon, and downstream of the stop codon are also shown. The Aven DNA sequence has no significant homology to previously known sequences.

It will be appreciated by those skilled in the art that as a result of the degeneracy of the genetic code, a multitude of nucleotide sequences encoding Aven, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring Aven, and all such variations are to be considered as being specifically disclosed.

Although nucleotide sequences which encode Aven and its variants are preferably capable of hybridizing to the nucleotide sequence of the naturally occurring Aven under appropriately selected conditions of stringency, it may be advantageous to produce nucleotide sequences encoding Aven or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding Aven and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode Aven and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding Aven or any portion thereof.

Also encompassed by the invention are polynucleotide sequences that are capable of hybridizing to the claimed nucleotide sequences, and in particular, those shown in FIG. 2, under various conditions of stringency. Hybridization conditions are based on the melting temperature ($T_m$) of the nucleic acid binding complex or probe, and may be used at a defined stringency.

Altered nucleic acid sequences encoding Aven which are encompassed by the invention include deletions, insertions, or substitutions of different nucleotides resulting in a polynucleotide that encodes the same or a functionally equivalent Aven. The encoded protein may also contain deletions, insertions, or substitutions of amino acid residues which produce a silent change and result in a functionally equivalent Aven. Deliberate amino acid substitutions may be made on the basis of similarity in polarity, charge, solubility, hydrophobicity, hydrophilicity, and/or the amphipathic nature of the residues as long as the biological activity of Aven is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding Aven. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE™ (U.S. Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System (Gibco BRL, Gaithersburg, Md.). Preferably, the process is automated with machines such as the Hamilton Micro Lab 2200 (Hamilton, Reno, Nev.), Peltier Thermal Cycler PTC200 (MJ Research, Watertown, Mass.) and the ABI 377 DNA sequencers (Perkin Elmer).

The nucleic acid sequences encoding Aven may be extended utilizing a partial nucleotide sequence and employing various methods known in the art to detect upstream sequences such as promoters and regulatory elements. For example, restriction-site PCR uses universal primers to retrieve unknown sequence adjacent to a known locus. In this method, genomic DNA is first amplified in the presence of a linker primer and a primer specific to the known region.

The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. This method uses several restriction enzymes to generate a suitable fragment in the known region of a gene, which is then circularized by intramolecular ligation and used as a PCR template. Another method, known as capture PCR, involves PCR amplification of DNA fragments adjacent to a known sequence in human and yeast artificial chromosome DNA. In this method, multiple restriction enzyme digestions and ligations may also be used to place an engineered double-stranded sequence into an unknown portion of the DNA molecule before performing PCR. Additionally, one may use PCR, nested primers, and PROMOTERFINDER™ libraries (kit for finding unknown DNA sequences adjacent to a known sequence) to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ (automated fluorescent microsatelite analysis software) and SEQUENCE NAVIGATOR™ (sequence viewing software), Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode Aven, or fusion proteins or functional equivalents thereof, may be used in recombinant DNA molecules to direct expression of Aven in appropriate host cells. Due to the inherent degeneracy of the genetic code, other DNA sequences which encode substantially the same or a functionally equivalent amino acid sequence may be produced and these sequences may be used to clone and express Aven.

As will be understood by those of skill in the art, it may be advantageous to produce Aven-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter Aven encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding Aven may be ligated to a heterologous sequence to encode a fusion protein. For example, to screen peptide libraries for inhibitors of Aven activity, it may be useful to encode a chimeric Aven protein that can be recognized by a commercially available antibody. A fusion protein may also be engineered to contain a cleavage site located between the Aven encoding sequence and the heterologous protein sequence, so that Aven may be cleaved and purified away from the heterologous moiety.

In another embodiment, sequences encoding Aven may be synthesized, in whole or in part, using chemical methods well known in the art. Alternatively, the protein itself may be produced using chemical methods to synthesize the amino acid sequence of Aven, or a portion thereof. For example, peptide synthesis can be performed using various solid-phase techniques and automated synthesis may be achieved, for example, using the ABI 431 A Peptide Synthesizer (Perkin Elmer).

The newly synthesized peptide may be substantially purified by preparative high performance liquid chromatography. The composition of the synthetic peptides may be confirmed by amino acid analysis or sequencing (e.g., via the Edman degradation procedure). Additionally, the amino acid sequence of Aven, or any part thereof, may be altered during direct synthesis and/or combined using chemical methods with sequences from other proteins, or any part thereof, to produce a variant polypeptide.

Recombinant DNA molecules that are useful in preparing a biologically active Aven are also provided. Preferred recombinant DNA molecules are characterized by a DNA sequence selected from the sequence shown in FIG. 2, cloning or expression vectors containing a sequence encoding a recombinant protein or polypeptide of the present invention, as described above, DNA sequences that hybridize to any of those DNA sequences and that code for Aven, and DNA sequences which are degenerate as a result of the genetic code to the aforementioned DNA sequences and which code for an antigen of Aven.

The appropriate DNA sequence may be inserted into any of a wide variety of expression vectors by a variety of procedures, generally through use of an appropriate restriction endonuclease site. Suitable vectors include, for example, vectors consisting of segments of chromosomal, non-chromosomal and synthetic DNA sequences, such as various known derivatives of SV40, known bacterial plasmids, e.g., plasmids from *E. coli* including col E1, pCR1, pBR322, pMB9 and their derivatives, wider host range plasmids, e.g., RP4, cauliflower mosaic virus (CMV), tobacco mosaic virus (TMV), phage DNAs, e.g., the numerous derivatives of phage λ, e.g., NM 989, and other DNA phages such as M13 or filamentous single stranded DNA phages, yeast plasmids such as the $2\mu$ plasmid or derivatives thereof, viral DNA such as baculovirus, vaccinia, adenovirus, fowl pox virus, or pseudorabies, cosmids, pGEX vectors (Promega, Madison, Wis.), *Autographa californica* nuclear polyhedrosis virus (in an insect host such as *Spodoptera frugiperda* or Trichoplusia larvae), and vectors derived from combinations of plasmids and phage DNAs, such as plasmids which have been modified to employ phage DNA or other expression control sequences.

Within each specific cloning or expression vehicle, various sites may be selected for insertion of the DNA sequences of this invention. These sites are usually designated by the restriction endonuclease which cuts them and there are various known methods for inserting DNA sequences into these sites to form recombinant DNA molecules. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment, and that insertion may occur by alternative means.

For expression of the DNA sequences of this invention, these DNA sequences are operatively linked to one or more expression control sequences in the expression vector. Such operative linking, which may be effected before or after the chosen DNA sequence is inserted into a cloning vehicle, enables the expression control sequences to control and promote the expression of the inserted DNA sequence.

Any of a wide variety of expression control sequences—sequences that control the expression of a DNA sequence when operatively linked to it—may be used in these vectors to express the DNA sequences of this invention. Such useful expression control sequences include, for example, the early and late promoters of SV40, the lac or trp systems, the hybrid lacZ promoter of the BLUESCRIPT™ phagemid (Stratagene, La Jolla, Calif.) or PSPORT1™ plasmid (Gibco BRL), the TAC or TRC system, the major operator and promoter regions of phage λ, the control regions of fd coat protein, the baculovirus polyhedrin promoter, promoters of human cytomegalovirus, the promoter for 3-phosphoglycerate kinase or other glycolytic enzymes, the promoters of acid phosphatase, e.g., Pho5, the 35S and 19S promoters of CMV, the omega leader sequence of TMV, the late promoter and tripartite leader sequence of adenovirus, the promoters of the yeast α-mating factors, alcohol oxidase, and PGH, promoters derived from plant cell genomes, e.g., heat shock, Rubisco, and storage protein genes, and other sequences known to control the expression of genes in prokaryotic or eukaryotic cells or their viruses, and various combinations thereof.

The expression vector also includes a non-coding sequence for a ribosome binding site for translation initiation and a transcription terminator. In mammalian cell systems, promoters from mammalian genes or mammalian viruses are preferable as well as altered 3' non-coding sequences.

The vector may also include appropriate sequences for amplifying expression. In mammalian cells, it is additionally possible to amplify the expression units by linking the gene to that coding for dehydrofolate reductase and applying a selection to host Chinese hamster ovary (CHO) cells. Many other genes have been used for chromosomal amplification including glutamine synthetase. If it is necessary to generate a mammalian cell line that contains multiple non-chromosomal copies of the sequence encoding Aven, vectors based on SV40 or EBV may be used with an appropriate selectable marker.

The vector or expression vehicle, and in particular the sites chosen therein for insertion of the selected DNA fragment and the expression control sequence employed in this invention are determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site is determined by a balance of these factors, not all selections being equally effective for a given case.

Specific initiation signals may also be used to achieve more efficient translation of sequences encoding Aven. Such signals include the ATG initiation codon and adjacent sequences. In cases where sequences encoding Aven, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of transcriptional enhancers, such as the SV40, CMV (cytomegalovirus) and RSV (rouse sarcoma virus) enhancers, which are appropriate for the particular cell system which is used.

The recombinant DNA molecule containing the desired gene operatively linked to expression control sequences may then be employed to transform a wide variety of appropriate hosts so as to permit such hosts (transformants) to express the gene, or fragment thereof, and to produce the polypeptide, or portion thereof, for which the hybrid DNA codes. The recombinant DNA molecule may also be employed to transform a host so as to permit that host on replication to produced additional recombinant DNA molecules as a source of Aven genes and fragments thereof.

A wide variety of hosts are also useful in producing the DNA sequences of this invention. These hosts include, for example, bacteria such as *E. coli*, Bacillus and Streptomyces, fungi such as yeasts, insect cell systems, plant cells, and animal cells such as CHO, HeLa, MDCK, HEK293, and WI38. The selection of an appropriate host for either of these uses is controlled by a number of factors. These include, for example, compatibility with the chosen vector, toxicity of the co-products, ease of recovery of the desired polypeptide, expression characteristics, biosafety and costs. No absolute choice of host may be made for a particular recombinant DNA molecule or polypeptide from any of these factors alone. Instead, a balance of these factors must be struck with the realization that not all hosts may be equally effective for expression of a particular recombinant DNA molecule.

It is also understood that the DNA sequences that are inserted at the selected site of a cloning or expression vehicle may include nucleotides which are not part of the actual gene coding for the desired polypeptide or may include only a fragment of the entire gene for that protein. It is only required that whatever DNA sequence is employed, the transformed host produces a polypeptide having the biological activity of native Aven. The transformed host may also express other proteins or compounds in addition to a Aven polypeptide. For example, a transformed host may be designed to express Aven and another compound such as a monoclonal antibody or other recombinant protein of interest, or to express both Aven and Bcl-$x_L$. Such host cell lines may have significant clinical or biological uses in producing compounds of interest to scientists.

For example, the DNA sequences of this invention may be fused in the same reading frame in an expression vector of this invention to a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired DNA sequence, improve purification or permit secretion, and preferably maturation, of the desired polypeptide from the host cell. The DNA sequence may alternatively include an ATG start codon, alone or together with other codons, fused directly to the sequence encoding the first amino acid of a desired polypeptide. Such constructions enable the production of, for example, a methionyl or other peptidyl polypeptide that is part of this invention. This N-terminal methionine or peptide may then be cleaved intra- or extra-cellularly by a variety of known processes or the polypeptide used together with the methionine or other fusion attached to it in the compositions and methods of this invention.

The appropriate DNA sequence present in the vector when introduced into a host may express part or only a portion of the protein which is encoded, it being sufficient that the expressed protein be capable of eliciting the same biological activity as the amino acid sequence depicted in FIG. 1. For example, in employing *E. coli* as a host organism, the UGA codon is a stop codon so that the expressed protein may only be a fragment of the antigen encoded into the vector and for this reason it is generally preferred that all of the UGA codons in the appropriate DNA sequence be converted into non-stop codons. Another way around the problem in a host that recognizes UGA as a stop codon is to include an additional DNA sequence which encodes a t-RNA which translates the UGA codon within a protein coding sequence as tryptophan in the transformed organism.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, ubiquitination, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express Aven may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase and adenine phosphoribosyltransferase genes which can be employed in tk or aprt cells, respectively. Also, antimetabolite, antibiotic or herbicide resistance can be used as the basis for selection; for example, dhfr which confers resistance to methotrexate; npt (neomycin phosphotransferase), which confers resistance to the aminoglycosides neomycin and G-418; and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine. In additional to genes used for selection, visible markers such as anthocyanins, beta glucuronidase and its substrate GUS, and luciferase and its substrate luciferin, can be used not only to identify transformants, but also to quantify the amount of transient or stable protein expression attributable to a specific vector system.

Although the presence/absence of marker gene expression suggests that the gene of interest is also present, its presence and expression may need to be confirmed. For example, if the sequence encoding Aven is inserted within a marker gene sequence, recombinant cells containing sequences encoding Aven can be identified by the absence of marker gene function. Alternatively, a marker gene can be placed in tandem with a sequence encoding Aven under the control of a single promoter. Expression of the marker gene in response to induction or selection usually indicates expression of the tandem gene as well.

Alternatively, host cells which contain the nucleic acid sequence encoding Aven and express Aven may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

Figure 4:
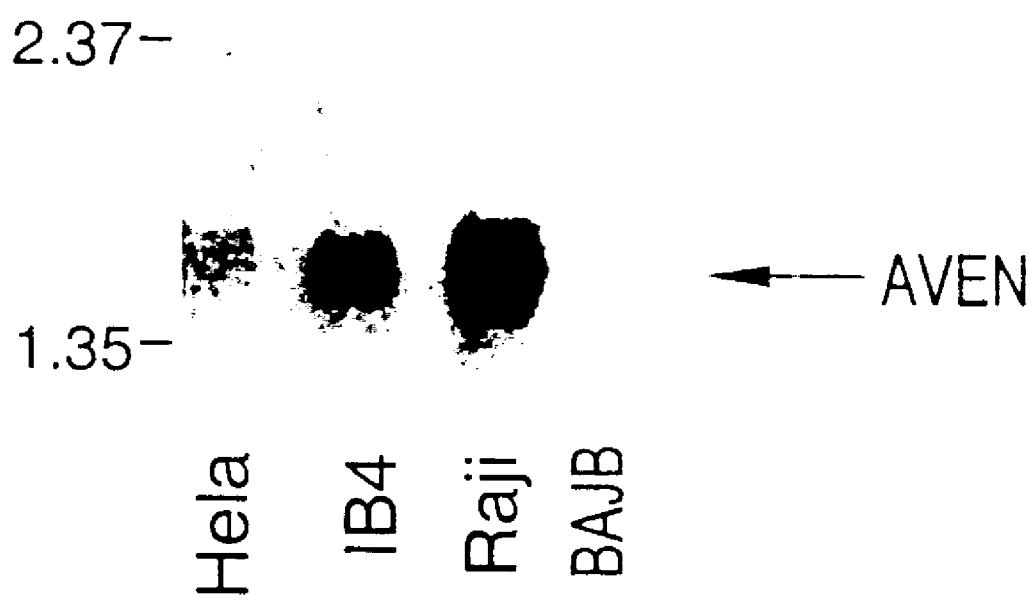
FIG. 4 is a Northern blot of different cell lines.

FIG. 3 depicts the result of a Northern blot analysis performed to determine whether Aven is expressed in a variety of tissue types. The results shown in FIG. 3 indicate that Aven is expressed in a wide variety of adult tissue, and is prominently expressed in reproductive tissue. Northern blot analysis was also performed with mRNA isolated from HeLa, IB4, and Raji cell lines, and the results are shown in FIG. 4. Both in tissues and cell lines, only a single 1.7 kb RNA species was detected, consistent with the size of the cDNA clone that extends 1526 nucleotides from the 5' end to the beginning of the polyA.

Figure 5:
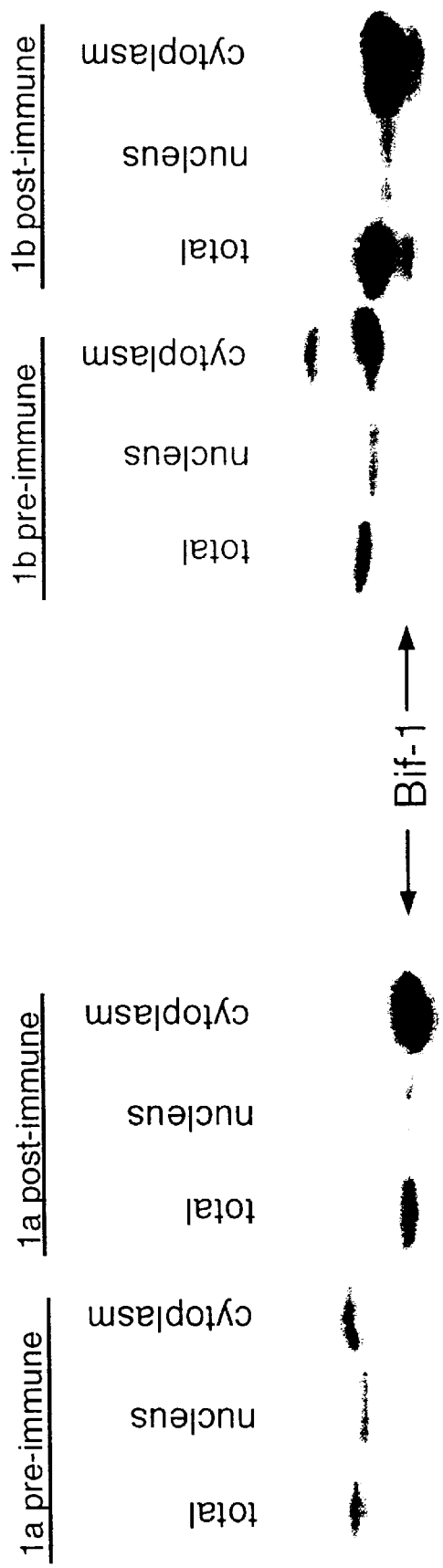
FIG. 5 is a Western blot analysis illustrating the probing of endogenous Aven from Raji cell lysate with polyclonal anti-peptide antibodies. The majority of Aven is localized in the cytoplasmic cell fraction.

To confirm the expression of Aven in cells, a Western blot analysis was performed on Raji cell lysate with polyclonal antibodies to Aven, as shown in FIG. 5. The antibodies, named αAvena and αAvenb, were generated against two peptides corresponding to residues 98–112 and residues 256–268, respectively, of the amino acid sequence shown in FIG. 1. The Raji cell lysate was separated into nuclear and cytoplasmic fractions prior to analysis. As shown in FIG. 5, Aven is predominantly localized in the cytoplasm, but can also be found in the nucleus. Aven mutations of three leucines 190, 192 and 194 to Alanine caused a redistribution of Aven to the nucleus from the cytosol demonstrating that this region may encode a nuclear export signal. These mutations enhanced the anti-apoptotic function of Aven in hippocampal neurons in culture, demonstrating that a nuclear function is important for anti-apoptotic activity in at least neurons.

Figure 7B:
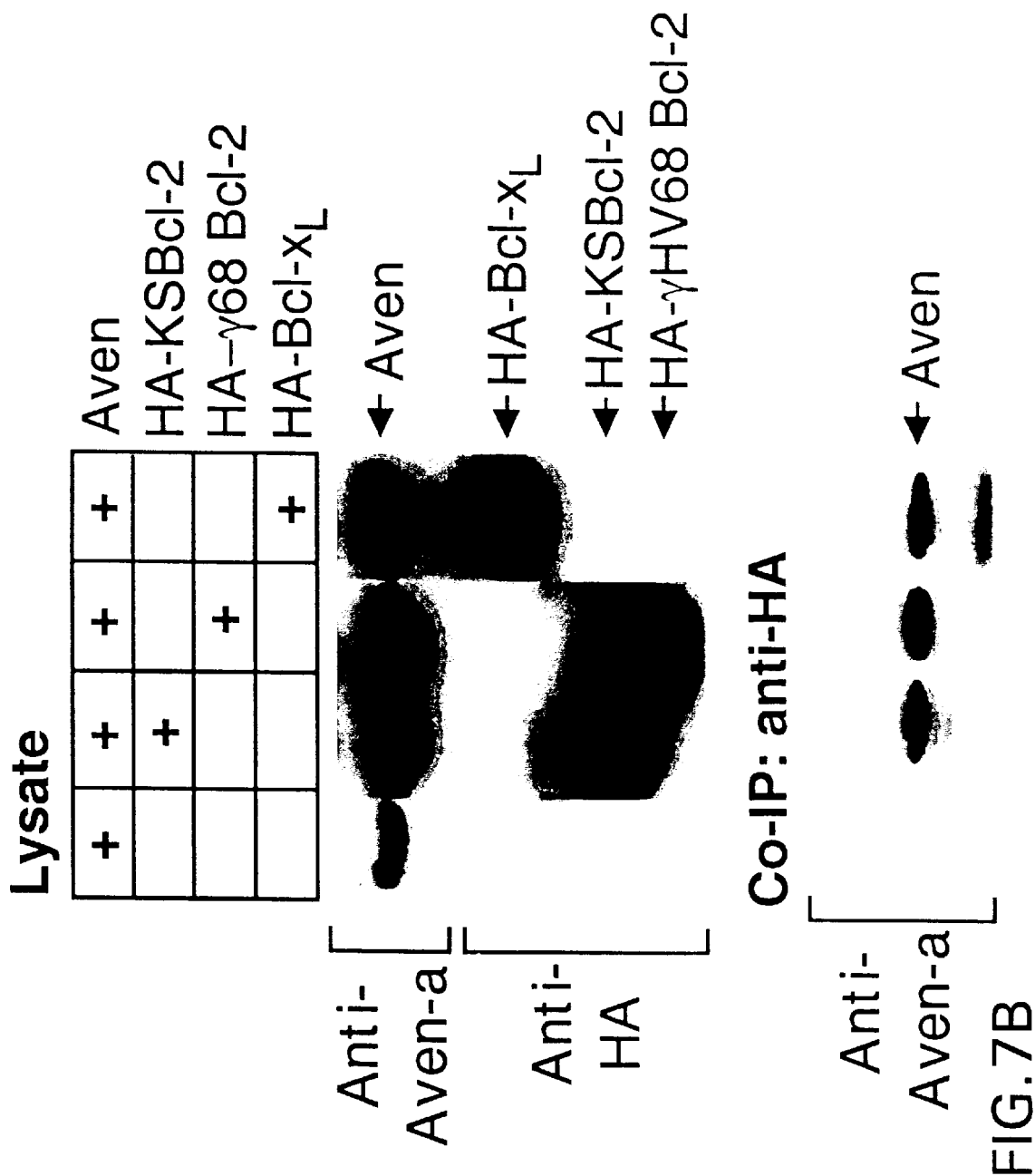
FIG. 7B shows the interaction between Aven and Bcl-2 family members.
Figure 8A:
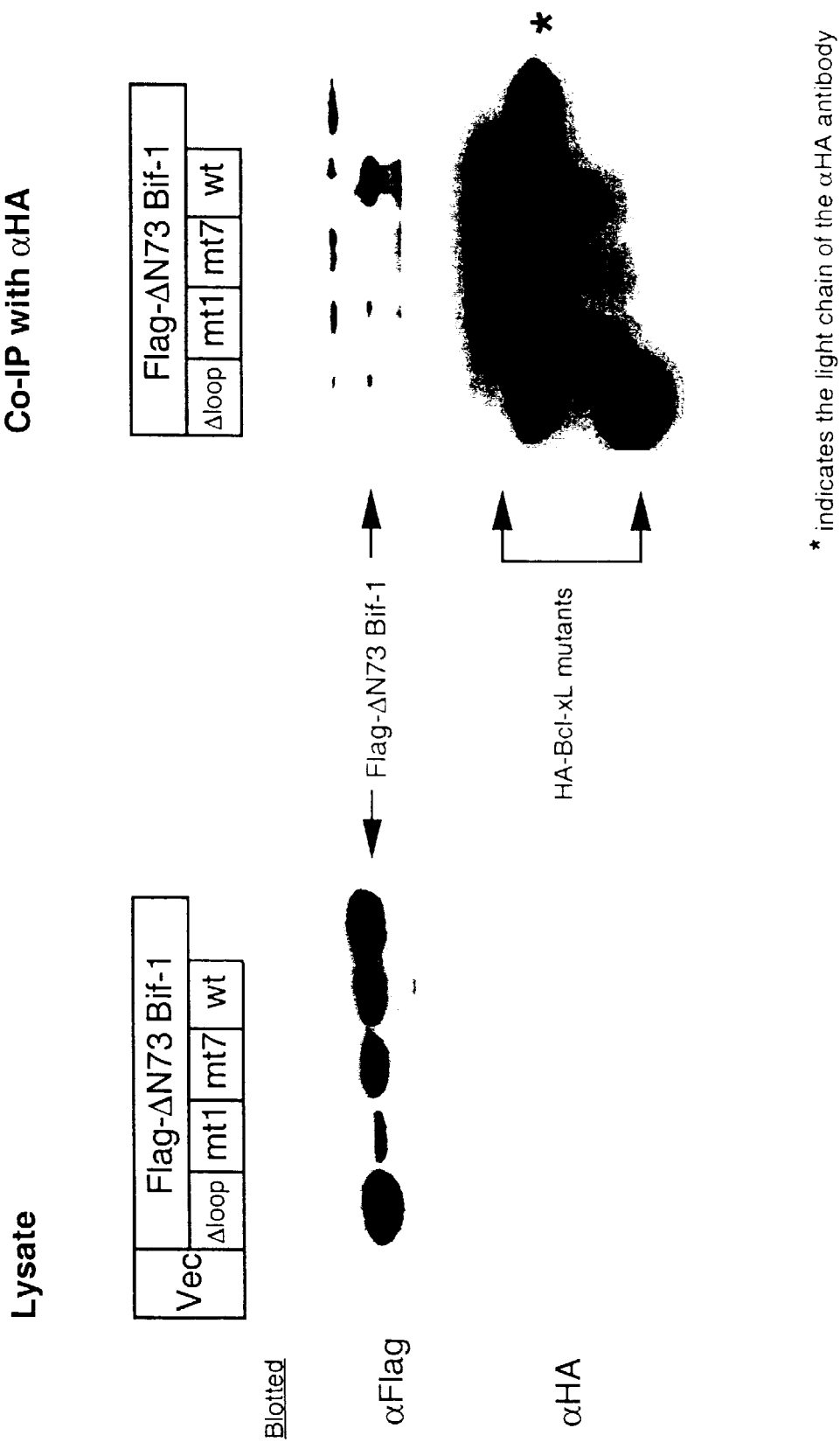
FIG. 8A is a co-immunoprecipitation analysis showing that Aven interacts with functional Bcl-$x_L$.
Figure 8B:
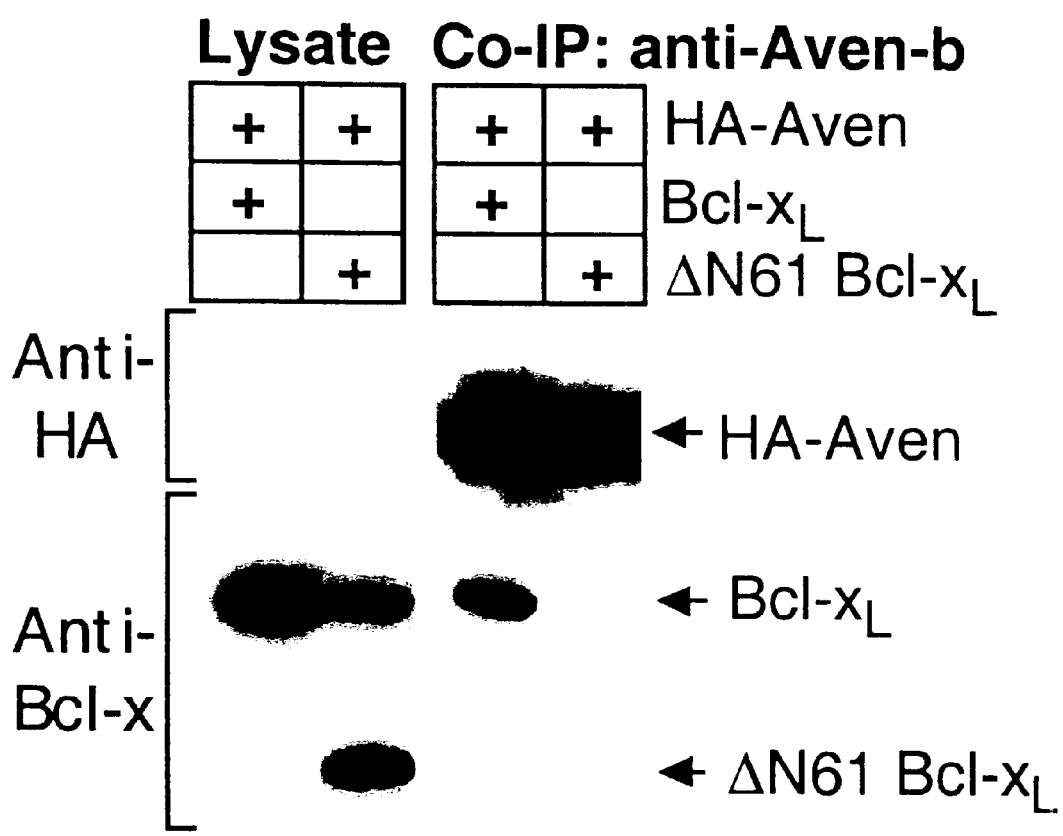
FIG. 8B shows the interaction between Aven and Bcl-2 family members.

FIGS. 6, 7, and 8 depict the result of yeast two-hybrid and co-immunoprecipitation analyses performed on COS-1 cell lysates to determine the ability of Aven to interact with other Bcl-2 family members. The constructs included in the transfection are indicated as a (+) (FIGS. 6, 7, and 8). The immunoprecipitating antibodies (top) and immunoblotting antibodies (side) are indicated (FIGS. 7 and 8). Anti-apoptotic proteins such as Bcl-2 (FIG. 6), Bcl-$x_L$ (FIGS. 6, 7, 8), KSBcl-2 (Kaposi sarcoma-associated herpes virus Bcl-2 homologue) (FIGS. 6, 7B), and Bcl-$x_L$ mt1 (FIGS. 6, 8A)(a mutant retaining anti-apoptotic activity) interact with Aven (FIG. 8B). Aven does not interact with pro-apoptotic proteins such as Bax and Bak, however, as shown in FIG. 6.

It is also noteworthy that Aven has significantly higher affinity with Bcl-$x_L$ than with Bcl-2 or KSBcl-2 (FIG. 7B). Because the full length Aven would be masked by the heavy chain of the immunoprecipitating antibody, HA epitope tagged Bcl-$x_L$ and its mutants were co-transfected with Flag epitope-tagged N-terminal deletion Aven. (FIG. 8A). As can be seen in FIGS. 7A, 7B and 8B, Aven did not interact with pro-apoptotic N-terminal truncation Bcl-$x_L$ (FIG. 7A) or the non-functional mutant mt7 (FIG. 8A), but did interact with the functional loop deletion and mt1 mutants (FIG. 8A), suggesting that Aven may be a common downstream effector that relays the anti-apoptotic activity of Bcl-2 family members.

Figure 9A:
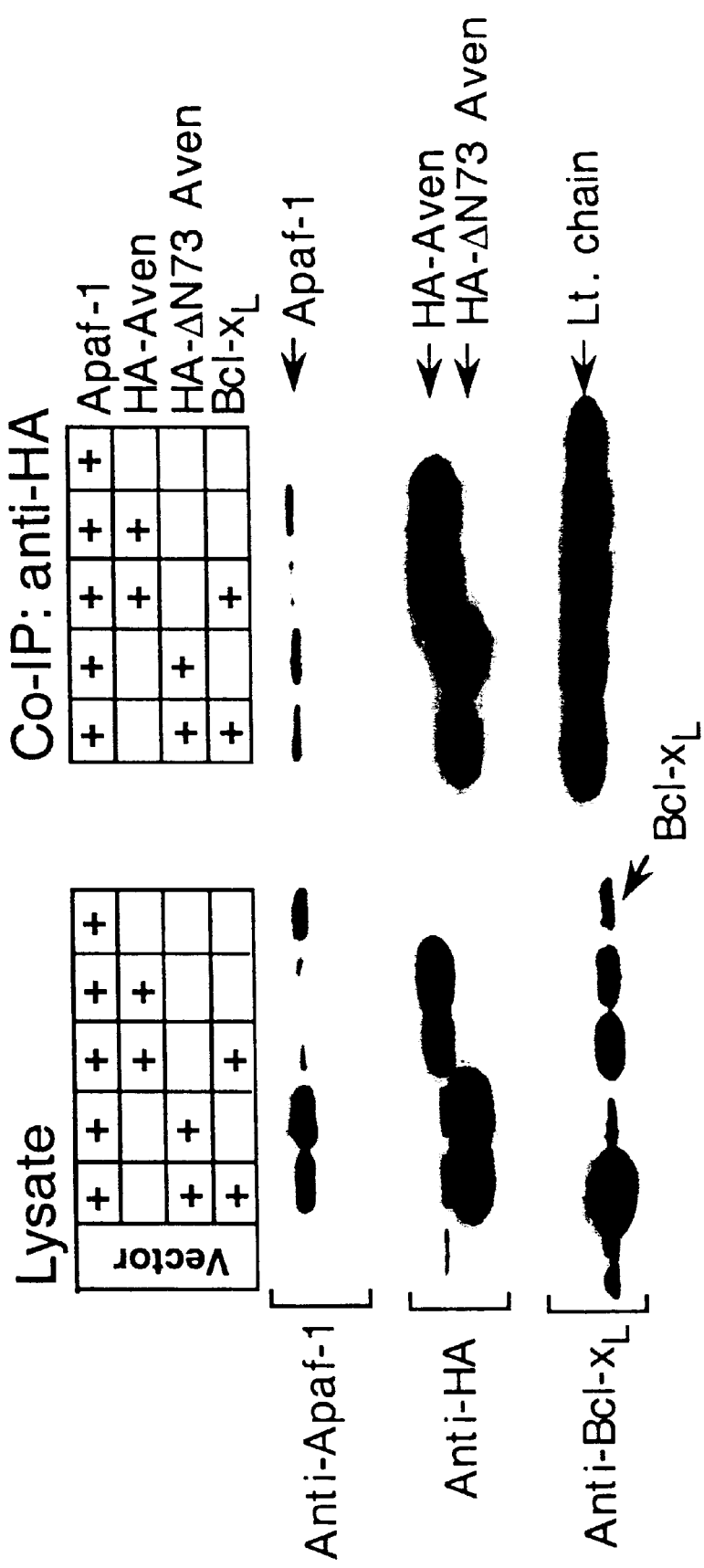
Figure 9F:
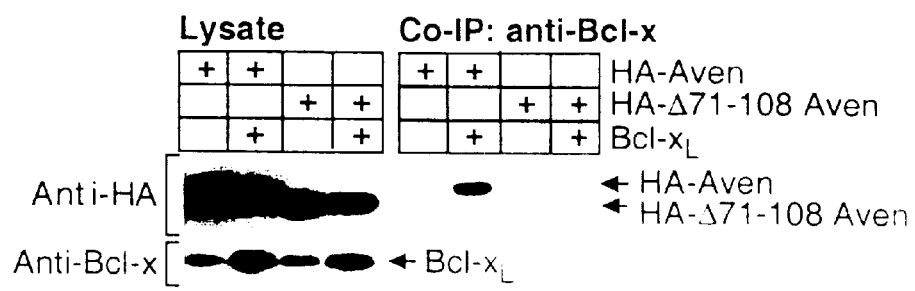
FIGS. 9F–J show that the interaction between Aven and Apaf-1 is independent of Bcl-xL.
Figure 9G:
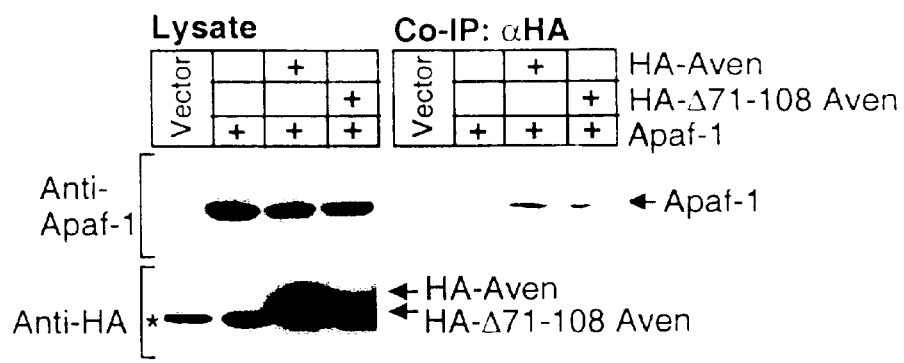
Figure 9H:
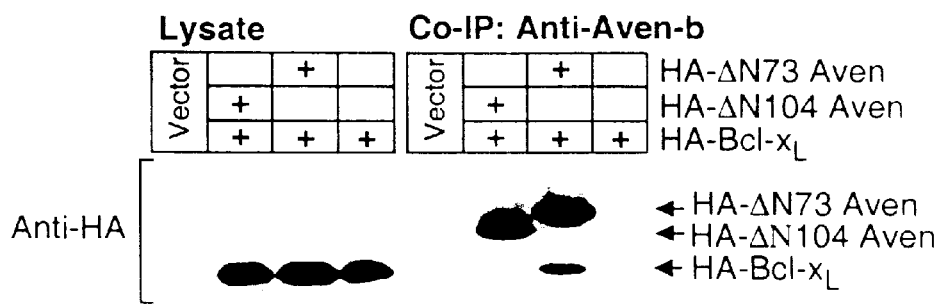
Figure 9I:
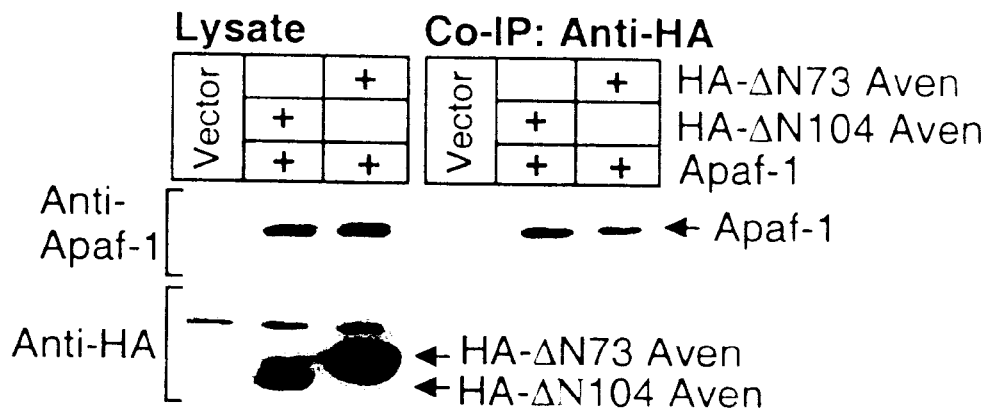
Figure 9J:
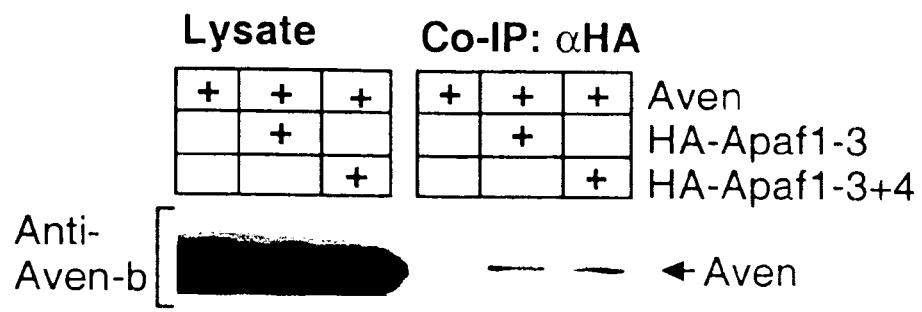

FIGS. 9A–E shows the interaction between Aven and Apaf-1. HA epitope-tagged full length Aven and HA-tagged ΔN73 Aven were co-transfected with Apaf-1 in the presence or absence of human Bcl-xL (hBcl-xL) into COS-1 cells, and cell lysates were precipitated with anti-HA antibody. Both full length and truncated Aven were able to interact with Apaf-1 in either the presence or absence of transfected hBcl-xL (FIG. 9A). The ability of N-terminal-truncated Aven to interact with Apaf-1, eliminated the possibility of a false positive due to the potentially "sticky" arginine-rich region of Aven. To eliminate the possibility of a non-specific interaction between Apaf-1 and the HA-antibody, anti-Aven antibodies were used to perform the co-immunoprecipitation experiment. HA epitope-tagged Apaf-1 was co-immunoprecipitated with Aven by both of the Aven antibodies (FIG. 9B and data not shown). Using a reverse strategy, precipitation of HA-Apaf-1 with anti-HA antibody co-precipitated Aven (FIG. 9C).

To verify that endogenous Apaf-1 and Aven proteins can interact, Hela cell lysates were immunoprecipitated with pre- or post-immune anti-Aven-a serum and immunoblotted with polyclonal anti-Apaf-1 antibody (provided by X. Wang). Only the post-immune serum and not the control serum co-precipitated endogenous Apaf-1 with Aven (FIG. 9D). Similarly, only post-immune anti-Aven-b serum co-precipitated Apaf-1 from 293T cell extracts. Apaf-1 was detected with a monoclonal anti-Apaf-1 antibody (provided by Y. Lazebnik) (FIG. 9E). Thus, two different Aven antibodies co-precipitated endogenous Apaf-1 from two different cell types.

FIGS. 9F–J demonstrate that Aven interacts with Apaf-1 independently of Bcl-xL. Co-immunoprecipitation experiments were performed on transfected cells as described for FIGS. 9A–E above.

Figure 10A:
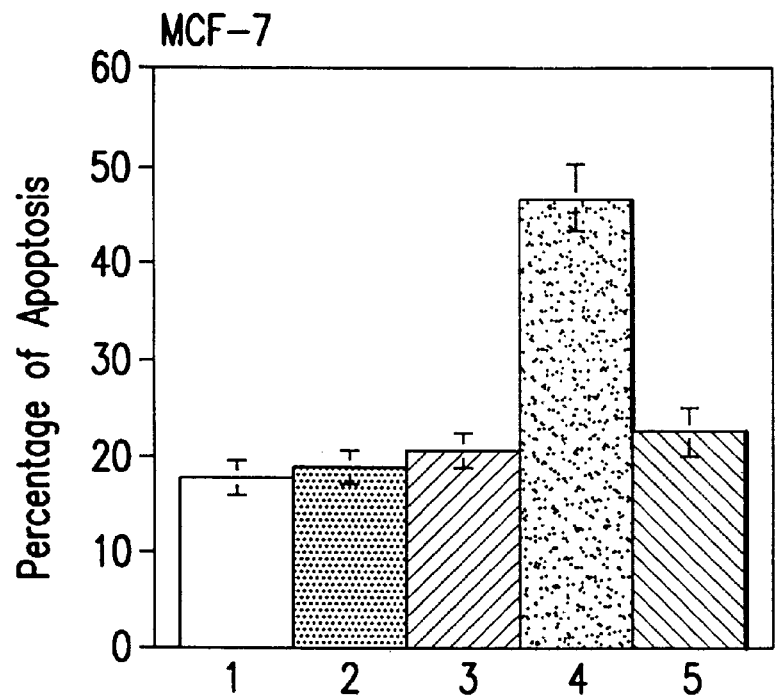
FIGS. 10(a)–(c) are bar charts depicting the percentage of apoptosis induced by co-transfection of caspase-9 and Apaf-1 in three different cell lines. The addition of Aven inhibited apoptosis.
Figure 10B:
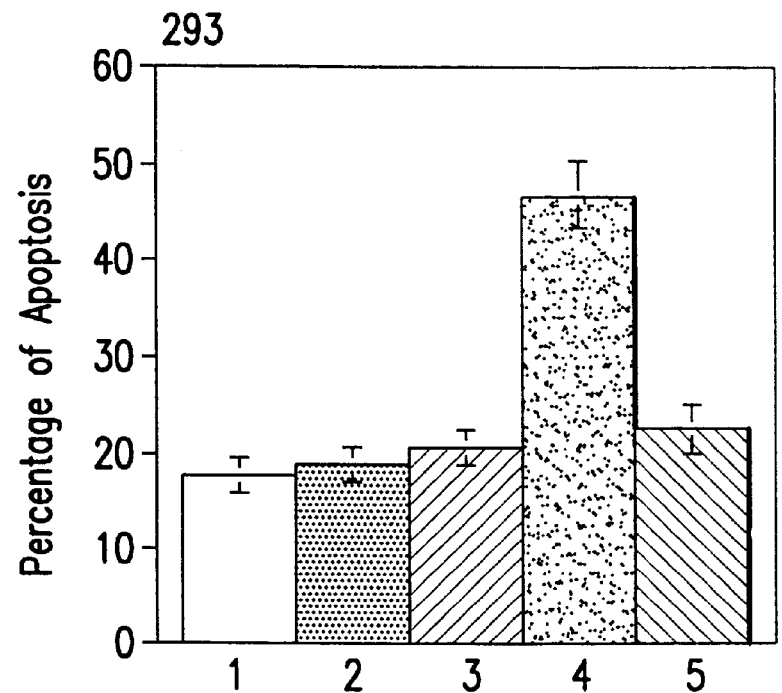
Figure 10C:
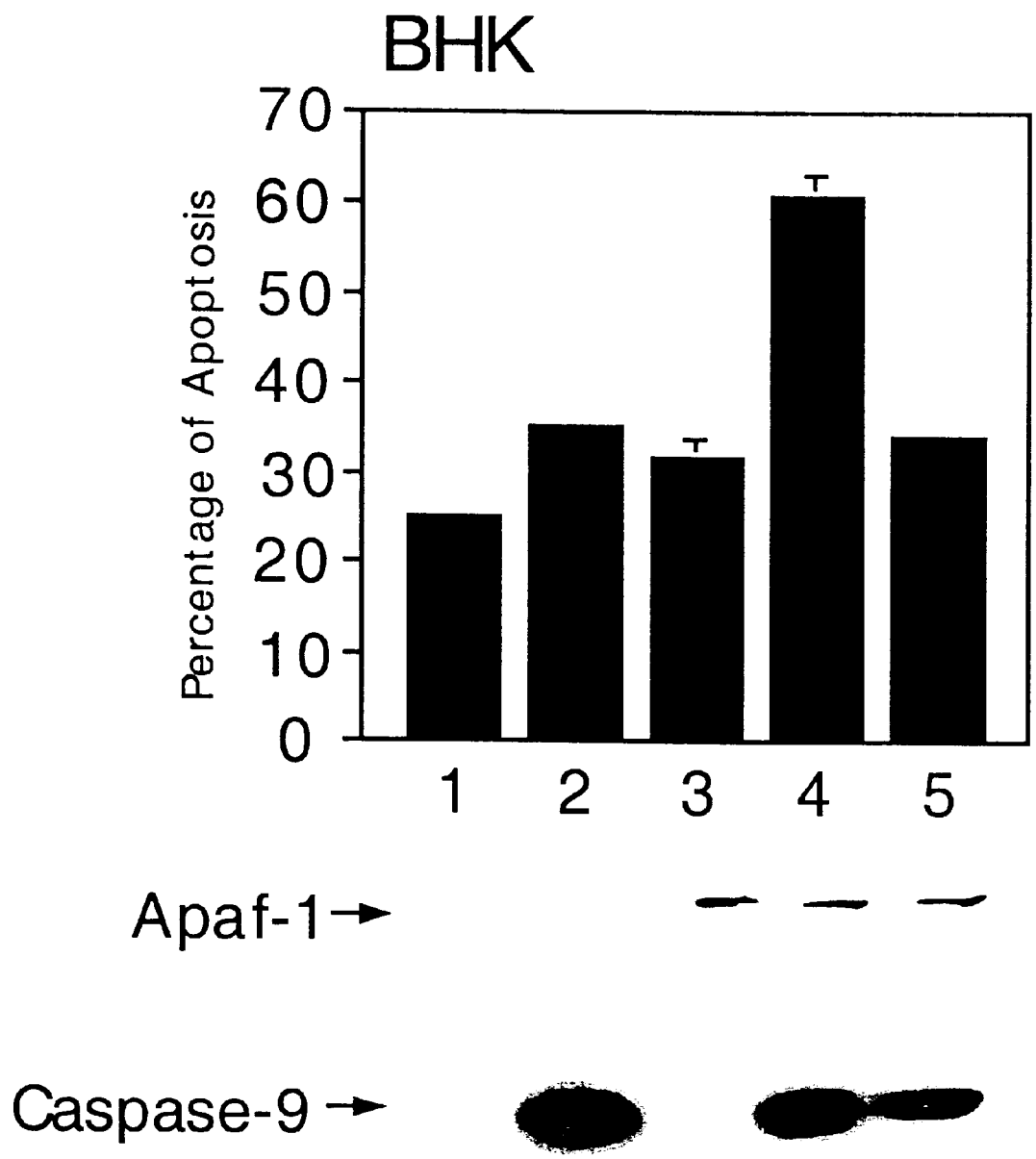

FIGS. 10(a)–(c) depict the results of Aven presence on apoptosis in three different cell lines. Numeral 1 indicates vector control, 2 indicates caspase-9, 3 indicates Apaf-1, 4 indicates caspase-9 plus Apaf-1, and 5 indicates caspase-9, Apaf-1 and Aven. Aven was co-transfected with Apaf-1 and caspase-9 using beta-galactosidase as a marker of transfection. Neither Apaf-1 (3) or caspase-9 (2) alone induced cell death, but co-transfection of Apaf-1 and caspase 9 (4) resulted in cell death. Addition of Aven to the Apaf-1/caspase-9 co-transfection (5) significantly decreased the percentage of cell death in all three cell types. FIG. 10(c) also includes a Western blot result of BHK cell lysates, performed in order to eliminate the possibility of differential protein expression, showing that comparable amounts of Apaf-1 and caspase-9 were expressed regardless of the presence of Aven.

Figure 11:
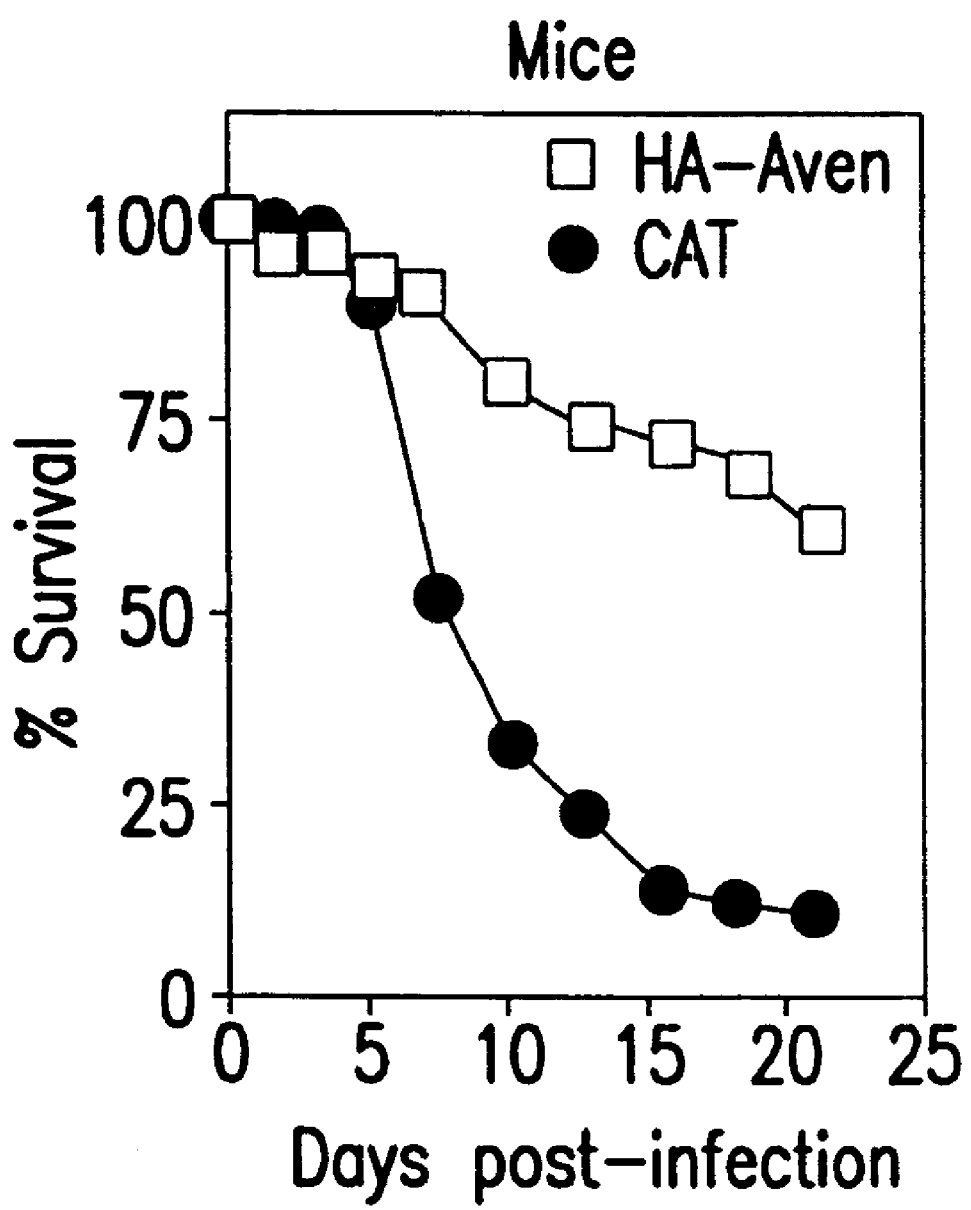
FIG. 11 demonstrates the in vivo protective effect of Aven against Sindbis virus infection and neuronal apoptosis in mice.

Aven protects mice against Sindbis virus infection and neuronal apoptosis as shown in FIG. 11. Aven inhibits apoptosis and enhances the anti-apoptotic function of Bcl-xL. Sindbis virus, a neurovirulent alphavirus, specifically infects central nervous system neurons and induces apoptosis with a fatal consequence in newborn mice (Lewis et al. (1996), J.Virol. 70, 1828–1835., incorporated by reference herein). Bcl-2 family members expressed from the recombinant Sindbis virus vector protect mice from neuronal apoptosis and fatal disease (Levine et al., (1996), Proc. Natl. Acad. Sci. USA 93, 4810–4815; Lewis et al., (1999), Nature Medicine 5, 832–835, both incorporated by reference herein).

To determine if Aven blocks neuronal apoptosis in vivo, recombinant Sindbis viruses expressing Aven or a control protein, CAT (chloramphenicol acetyl-transferase), were injected intracranially into mice. Mortality was monitored for twenty-one days post infection. Animals infected with Aven-expressing virus survived significantly better (60%) than mice infected with the control virus (10%), demonstrating that Aven exhibits a protective function against neuronal apoptosis in vivo.

FIG. 12 demonstrates increased resistance to apoptosis induced by IL-3 withdrawl in pooled FL5.12 cells stably expressing Aven. To determine if Aven could protect against cell death induced by another physiologic death stimulus, pooled FL5.12 cells stably expressing Aven were tested for resistance to apoptosis induced by IL-3 withdrawal. The data are presented as mean (+/–SEM) for three independent experiments. At all time points tested, cells expressing Aven had approximately 20% higher viabilities (FIG. 12A).

Immunoblot analysis of pooled FL5.12 cells stably expressing Aven or control vector using anti-Aven-b serum is shown in FIG. 12B. The "*" indicates a non-specific band while the "←" arrow marks the position of Aven. Immunoblot analysis confirmed overexpression of Aven in the pooled Aven-transfected cells but not in vector-transfected cells.

Figure 13:
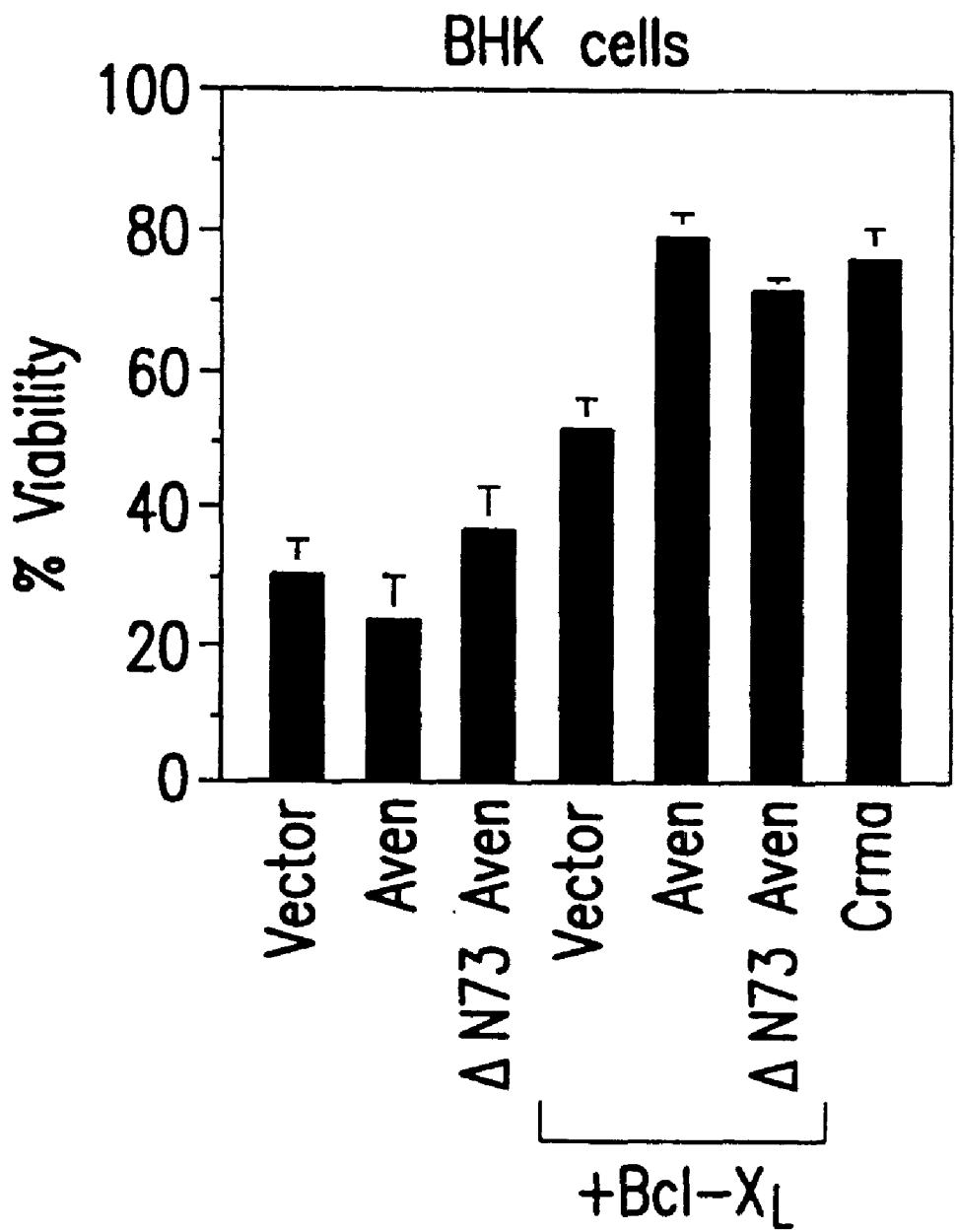
FIG. 13 shows that Aven enhances the anti-apoptotic activity of Bcl-xL in BHK cells by 20–30%.

FIG. 13 shows that Aven enhances the anti-apoptotic activity of Bcl-xL by 20–30%. Bcl-xL protected cultured BHK (baby hamster kidney) cells from caspase-1-induced apoptosis by approximately 20%. Aven and an N-terminal truncated Aven (ΔN73) enhanced the anti-apoptotic activity of Bcl-xL by 20–30%. Thus, the two proteins together work about as well as the specific caspase-1 inhibitor CrmA, a potent anti-apoptotic agent. These findings demonstrate that the interaction between Aven and Bcl-xL enhances cell survival.

Figures 14A, 14B:
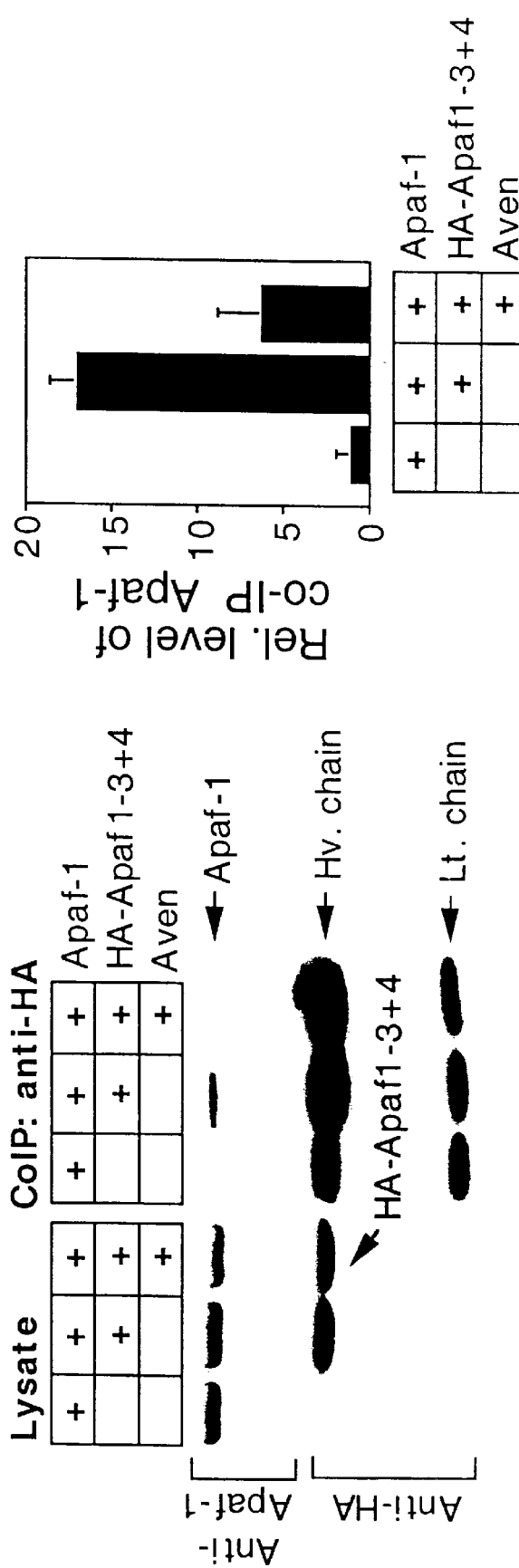
FIGS. 14A and 14B demonstrate that Aven inhibits self-association of Apaf-1.

FIGS. 14A and 14B demonstrate that Aven inhibits self-association of Apaf-1. Apaf-1 binds caspase-9 via its CED-3 homology domain, and Apaf-1 associates with itself to form oligomers through its CED-4-homology domain (Hu et al., 1999; Saleh et al., 1999; Zou et al., 1999 each incorporated by reference herein). Current evidence indicates that the self-association of Apaf-1 orients procaspase-9 molecules into close proximity and facilitates auto- or cross-catalytic activation of caspase-9, consequently activating the apoptotic program. Since Aven interacts with Apaf-1 and inhibits Apaf-1+caspase-9-induced apoptosis, the possibility that Aven could disrupt the self-association of Apaf-1 was tested. Aven inhibited co-immunoprecipitation of full length Apaf-1 with anti-HA antibody, demonstrating that Aven inhibits self-association of Apaf-1 (FIG. 14A). COS-1 cells were co-transfected with Apaf-1, HA-tagged CED-3+4 domains of Apaf-1 and Aven. Total cell lysates and anti-HA immunoprecipitates were immunoblotted with anti-Apaf-1 antibody.

Quantitation of co-precipitated Apaf-1 by densitometry in three independent experiments verified that Aven consistently decreased Apaf-1 self-association (FIG. 14B)

FIGS. 15A–D demonstrate that Aven inhibits the activation of caspases by cytochrome c and dATP in cell extracts. The transfection efficiency was optimized such that approximately 50% of the cells were transfected as determined by co-transfection with green fluorescence protein. Cytochrome c and dATP were added to the extracts at time zero and activation of endogenous caspase-9 and caspase-3 were monitored over time by immunoblot analysis to detect their active cleavage products.

Autoprocessing of endogenous caspase-9 to produce the active caspase-9 subunits was consistently impaired by Aven-containing extracts compared to control extracts (FIG. 15A). Similarly, Aven inhibited the processing of caspase-3, suggesting that impaired activation of caspase-9 resulted in the failure of caspase-9 to cleave pro-caspase-3 into its active subunits (FIG. 15B).

The same experiment described in FIGS. 15A and 15B was performed in COS-1 cells. Preparation of extracts from Aven- and control-transfected COS-1 cells produced identical results in this assay, further indicating that Aven inhibits activation of endogenous caspases (FIG. 15C and 15D).

Figure 16:
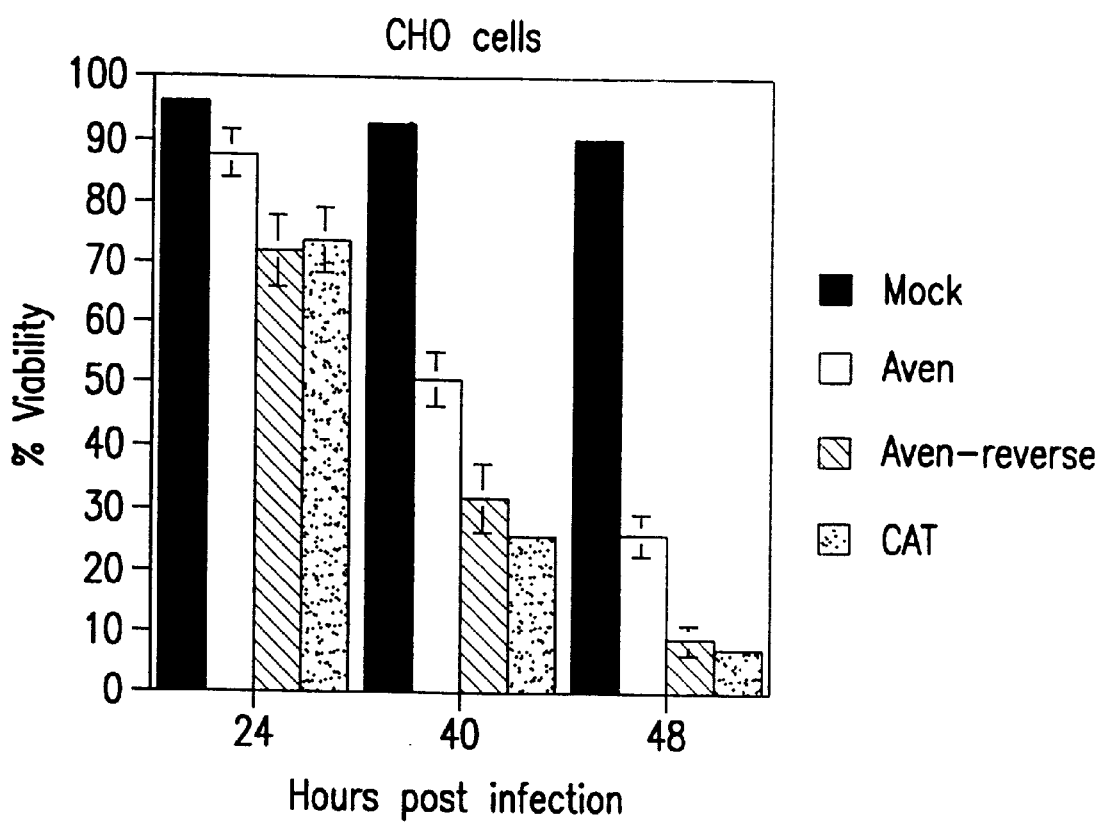
FIG. 16 demonstrates the protective effect of Aven in CHO cells infected with the Sindbis virus.

FIG. 16 demonstrates the protective effect of Aven in CHO cells infected with the Sindbis virus. Aven increased the percent viability of CHO cells in vitro by 20%. These results indicate that Aven can be used to extend the viability and useful life of in vitro cell cultures challenged with apoptotic-inducing events. Aven can be introduced into cells to protect against apoptotic-inducing events such as radiation, temperature, growth factor withdrawal, glucocorticoids and multiple classes of chemotherapeutic agents.

Extending the viability of cell cultures has many industrial applications in increasing the yield of production and lowering the costs of manufacturing of recombinantly expressed proteins and nucleic acids. For example, Aven or combinations of Aven, Bcl-$x_L$ and other cellular factors, can extend the viability of cell lines containing vectors expressing a protein of interest thereby increasing the recovery yield of recombinant protein. Increasing the recovery yield lower costs associated with the establishment of new cell lines and additional fermentations that would be necessary using less viable cells.

The presence of polynucleotide sequences encoding Aven can be detected by DNA-DNA or DNA-RNA hybridization or amplification using probes or portions or fragments of polynucleotides encoding Aven. Nucleic acid amplification based assays involve the use of oligonucleotides or oligomers based on the sequences encoding Aven to detect transformants containing DNA or RNA encoding Aven. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of Aven, using either polyclonal or monoclonal antibodies specific for the protein, are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on Aven is preferred, but a competitive binding assay may be employed.

A wide variety of labels and conjugation techniques are known by those skilled in the art and may be used in various nucleic acid and amino acid assays. Means for producing labeled hybridization or PCR probes for detecting sequences related to polynucleotides encoding Aven include oligolabeling, nick translation, end-labeling or PCR amplification using a labeled nucleotide. Alternatively, the sequences encoding Aven, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, Kalamazoo, Mich.; Promega; and U.S. Biochemical Corp.). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding Aven may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode Aven may be designed to contain signal sequences which direct secretion of Aven through a prokaryotic or eukaryotic cell membrane.

Other recombinant constructions may be used to join sequences encoding Aven to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and Aven may be used to facilitate purification.

One such expression vector provides for expression of a fusion protein containing Aven and a nucleic acid encoding 6 histidine residues preceding a thioredoxin or an enterokinase cleavage site. The histidine residues facilitate purification on IMIAC (immobilized metal ion affinity chromatography) while the enterokinase cleavage site provides a means for purifying Aven from the fusion protein.

In addition to recombinant production, fragments of Aven may be produced by direct peptide synthesis using solid-phase techniques. Protein synthesis may be performed using manual techniques or by automation. Automated synthesis may be achieved, for example, using Applied Biosystems 431A Peptide Synthesizer (Perkin Elmer). Various fragments of Aven may be chemically synthesized separately and combined using chemical methods to produce the full length molecule.

Based on the interaction of Aven with Bcl-$x_L$ and Apaf-1, Aven appears to play a role in diseases and disorders associated with aberrations in apoptosis regulation. These include the development of cancer, autoimmune diseases, lymphoproliferative disorders, atherosclerosis, AIDS, immunodeficiency diseases, ischemic injuries, neurodegenerative diseases, osteoporosis, myelodysplastic syndromes, toxin-induced diseases, and viral infections.

It has been demonstrated that Aven functions as an inhibitor of neuronal appoptosis in an animal model. When expressed from the Sindbis virus vector, Aven protects mice from a fatal Sindbis virus infection. Sindbis virus is a neurotropic virus that in the absence of Aven kills neurons of the central nervous system. Thus, Aven is a pro-survival factor in virus-infected neurons of the central nervous system in animals.

Therefore, in one embodiment, Aven or a fragment or derivative thereof may be administered to a subject to treat a disorder which is associated with increased apoptosis. Such conditions and diseases may include, but are not limited to, neurodegenerative diseases including Alzheimers', Parkinsons', and amyotrophic lateral sclerosis; myelodysplastic disorders such as aplastic anemia; ischemic injury due to stroke, trauma, and heart attacks, and AIDS.

In another embodiment, a vector capable of expressing Aven, or a fragment or a derivative thereof, may also be administered to a subject to treat the conditions described above.

In another embodiment, vectors expressing antisense of the nucleic acid sequence encoding Aven may be administered to a subject to treat a disorder which is associated with decreased apoptosis such as cancers, autoimmune diseases, and viral infections. Such disorders may include, but are not limited to, cancers of the brain and kidney; hormone-dependent cancers including breast, prostate, testicular, and ovarian cancers; lymphomas, leukemias; autoimmune disorders including systemic lupus erythematosus, scleroderma, and arthritis; and viral infections such as herpes, HIV, adenovirus, and HTLV-1 associated malignant disorders.

In one embodiment, antagonists or inhibitors of Aven may be administered to a subject to treat or prevent the cancers, autoimmune diseases and viral infections described above. In one aspect, antibodies which are specific for Aven may be used directly as an antagonist, or indirectly as a targeting or delivery mechanism for bringing a pharmaceutical agent to cells or tissue which express Aven.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of Aven may be produced using methods which are generally known in the art. In particular, purified Aven may be used to produce antibodies or to screen libraries of pharmaceutical agents to identify those which specifically bind Aven.

Antibodies may be generated using methods that are well known in the art. Such antibodies may include, but are not limited to, polyclonal, monoclonal, chimeric, humanized chimeric, naturalized, single chain, Fab fragments, and fragments produced by a Fab expression library. Neutralizing antibodies are especially preferred for therapeutic use.

For the production of antibodies, various hosts including goats, rabbits, rats, mice, humans, and others, may be immunized by injection with Aven or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to Aven have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of Aven amino acids may be fused with those of another protein such as keyhole limpet hemocyanin and antibody produced against the chimeric molecule.

Monoclonal antibodies to Aven may be prepared using any technique which provides for the production of antibody molecules by continuous cell lines in culture. These include, but are not limited to, the hybridoma technique, the human B-cell hybridoma technique, and the EBV-hybridoma technique.

In addition, techniques developed for the production of "chimeric antibodies," the splicing of mouse antibody genes to human antibody genes, may be used to obtain a molecule with appropriate antigen specificity and biological activity. Alternatively, techniques described for the production of single chain antibodies may be adapted, using methods known in the art, to produce Aven-specific single chain antibodies. Antibodies with related specificity, but of distinct idiotypic composition, may be generated by chain shuffling from random combinatorial immunoglobulin libraries. Antibodies may also be produced by inducing in vivo production in the lymphocyte population or by screening recombinant immunoglobulin libraries or panels of highly specific binding reagents.

Antibody fragments which contain specific binding sites for Aven may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between Aven and its specific antibody. A two-site, monoclonal-based immunoassay utilizing monoclonal antibodies reactive to two non-interfering Aven epitopes is preferred, but a competitive binding assay may also be employed.

In another embodiment of the invention, the polynucleotides encoding Aven, or any fragment thereof, or antisense molecules, may be used for therapeutic purposes. In one aspect, antisense to the polynucleotide encoding Aven may be used in situations in which it would be desirable to block the transcription of the mRNA. In particular, cells may be transformed with sequences complementary to polynucleotides encoding Aven. Thus, antisense molecules may be used to modulate Aven activity, or to achieve regulation of gene function. Such technology is now well known in the art, and sense or antisense oligomers or larger fragments, can be designed from various locations along the coding or control regions of sequences encoding Aven.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding Aven.

Genes encoding Aven can be turned off by transforming a cell or tissue with expression vectors which express high levels of a polynucleotide or fragment thereof which encodes Aven. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or other nucleic acids, to the control regions of the gene encoding Aven, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding Aven.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding Aven. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans. Aven RNA expression was detected in a wide variety of adult tissues and cell lines, implying that Aven is a ubiquitous factor. Aven homologues are found in the mouse, rat and rabbit EST databases, and human genome sequencing places Aven on chromosome 15. However, Aven lacks significant amino acid homology to previously identified proteins. The fact that human Aven protects mice from a fatal infection with the pro-apoptotic, neurotropic Sindbis virus also indicates that Aven function is conserved across species.

An additional embodiment of the invention relates to the administration of a pharmaceutical composition, in conjunction with a pharmaceutically acceptable carrier, for any of the therapeutic effects discussed above. Such pharmaceutical compositions may consist of Aven, antibodies to Aven, mimetics, agonists, antagonists, or inhibitors of Aven. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Mack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl cellulose, or sodium carboxymethyl cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of Aven, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example Aven or fragments thereof, antibodies of Aven, agonists, antagonists or inhibitors of Aven, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 10 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

In another embodiment, antibodies which specifically bind Aven may be used for the diagnosis of conditions or diseases characterized by expression of Aven, or in assays to monitor patients being treated with Aven, agonists, antagonists or inhibitors. The antibodies useful for diagnostic purposes may be prepared in the same manner as those described above for therapeutics. Diagnostic assays for Aven include methods which utilize the antibody and a label to detect Aven in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring Aven are known in the art and provide a basis for diagnosing altered or abnormal levels of Aven expression. Normal or standard values for Aven expression are established by combining body fluids or cell extracts taken from normal mammalian subjects, preferably human, with antibody to Aven under conditions suitable for complex formation. The amount of standard complex formation may be quantified by various methods, but preferably by photometric means. Quantities of Aven expressed in subject samples, control and disease from biopsied tissues are compared with the standard values. Deviation between standard and subject values establishes the parameters for diagnosing disease.

In another embodiment of the invention, the polynucleotides encoding Aven may be used for diagnostic purposes. The polynucleotides which may be used include oligonucleotide sequences, antisense RNA and DNA molecules, and other nucleic acids. The polynucleotides may be used to detect and quantitate gene expression in biopsied tissues in which expression of Aven may be correlated with disease. The diagnostic assay may be used to distinguish between absence, presence, and excess expression of Aven, and to monitor regulation of Aven levels during therapeutic intervention.

In one aspect, hybridization with PCR probes which are capable of detecting polynucleotide sequences, including genomic sequences, encoding Aven or closely related molecules, may be used to identity nucleic acid sequences which encode Aven. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding Aven, alleles, or related sequences.

Probes may also be used for the detection of related sequences, and should preferably contain at least 50% of the nucleotides from any of the Aven encoding sequences. The hybridization probes of the subject invention may be DNA or RNA and derived from the nucleotide sequence of FIG. 2 or from genomic sequence including promoter, enhancer elements, and introns of the naturally occurring Aven.

Means for producing specific hybridization probes for DNAs encoding Aven include the cloning of nucleic acid sequences encoding Aven or Aven derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or 35S, or enzymatic labels, such as alkaline phosphatase coupled to the probe via avidin/biotin coupling systems, and the like.

Polynucleotide sequences encoding Aven may be used for the diagnosis of conditions or diseases which are associated with expression of Aven. Examples of such conditions or diseases include cancers of the brain and kidney; hormone-dependent cancers including breast, prostate, testicular, and ovarian cancers; lymphomas, leukemias; autoimmune disorders including systemic lupus erythematosus, scleroderma and arthritis; and viral infections such as herpes, HIV, adenovirus, and HTLV-1 associated malignant disorders; neurodegenerative diseases including Alzheimers', Parkinsons', and amyotrophic lateral sclerosis; myelodysplastic disorders such as aplastic anemia; ischemic injury due to stroke, trauma, and heart attacks; and AIDS. The polynucleotide sequences encoding Aven may be used in Southern or Northern blot analysis, dot blot, or other membrane-based technologies; in PCR technologies; or in dip stick, pin, ELISA or chip assays utilizing fluids or tissues from patient biopsies to detect altered Aven expression. Such qualitative or quantitative methods are well known in the art.

In a particular aspect, the nucleotide sequences encoding Aven may be useful in assays that detect activation or induction of various cancers, particularly those mentioned above. The nucleotide sequences encoding Aven may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding Aven in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of Aven, a normal or standard profile for expression is established. This may be accomplished by combining body fluids or cell extracts taken from normal subjects, either animal or human, with a sequence, or a fragment thereof, which encodes Aven, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding Aven may involve the use of PCR. Such oligomers may be chemically synthesized, generated enzymatically, or produced from a recombinant source. Oligomers will preferably consist of two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of Aven include radiolabeling or biotinylating nucleotides, coamplification of a control nucleic acid, and standard curves onto which the experimental results are interpolated. The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequences which encode Aven may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries.

FISH may be correlated with other physical chromosome mapping techniques and genetic map data. Correlation between the location of the gene encoding Aven on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, Aven, its catalytic or immunogenic fragments or oligopeptides thereof, can be used for screening libraries of compounds in any of a variety of drug screening techniques. The fragment employed in such screening may be free in solution, affixed to a solid support, borne on a cell surface or located intracellularly. The formation of binding complexes between Aven and the agent being tested may be measured.

Another technique for drug screening which may be used provides for high throughput screening of compounds having suitable binding affinity to the protein of interest. In this method, as applied to Aven, large numbers of different small test compounds are synthesized on a solid substrate, such as plastic pins or some other surface. The test compounds are reacted with Aven, or fragments thereof, and washed. Bound Aven is then detected by methods well known in the art. Purified Aven can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding Aven specifically compete with a test compound for binding Aven. In this manner, the antibodies can be used to detect the presence of any peptide which shares one or more antigenic determinants with Aven.

In additional embodiments, the nucleotide sequences which encode Aven may be used in any molecular biology techniques that have yet to be developed, provided the new techniques rely on properties of nucleotide sequences that are currently known, including, but not limited to, such properties as the triplet genetic code and specific base pair interactions.

Application of the teachings of the present invention to a specific problem or environment is within the capabilities of one having ordinary skill in the art in light of the teachings contained herein. Examples of the products and processes of the present invention appear in the following examples.

EXAMPLE 1 cDNA Library Construction

The cDNA library is constructed from Raji cells. The frozen cells are homogenized and lysed using a Brinkmann Homogenizer Polytron PT-3000 (Brinkmann Instruments, Westbury, N.J.) in guanidinium isothiocyanate solution. The lysate is centrifuged over a 5.7M CsCl cushion using a Beckman SW28 rotor in a Beckman L8-70M Ultracentrifuge (Beckman Instruments) for 18 hours at 25,000 rpm at ambient temperature. The RNA is extracted with acid phenol pH 4.7, is precipitated using 0.3M sodium acetate and 2.5 volumes of ethanol, is resuspended in RNAse-free water, and is DNase treated at 37° C. The mRNA is then isolated using the QIAGEN OLIGOTEX (primer analysis software) kit (QIAGEN, Inc., Chatsworth, Calif.) and used to construct the cDNA library.

The mRNA is handled according to the recommended protocols in the SuperScript Plasmid System for cDNA Synthesis and Plasmid Cloning (Cat. #18248-013, Gibco BRL). A new plasmid is constructed using the following procedures: The commercial plasmid PSPORT1 (Gibco BRL) is digested with Eco RI restriction enzyme (New England Biolabs, Beverley, Mass.), the overhanging ends of the plasmid are filled with Klenow enzyme (New England Biolabs) and 2'-deoxynucleotide-5'-triphosphates (dNTPs), and the intermediate plasmid is self-ligated and transformed into the bacterial host, E. coli strain JM109.

Quantities of this intermediate plasmid are digested with HindIII restriction enzyme (New England Biolabs), the overhanging ends are filled with Klenow and dNTPs, and a 10-mer linker of sequence 5' . . . CGGAATTCCG . . . 3' (SEQ ID NO: 3) is phosphorylated and ligated onto the blunt ends. The product of the ligation reaction is digested with EcoRI and self-ligated. Following transformation into JM109 host cells, plasmids designated pINCY are isolated and tested for the ability to incorporate cDNAs using NotI and EcoRI restriction enzymes.

The cDNAs are fractionated on a Sepharose (agarose beads) CL4B column (Cat. #275105-01, Pharmacia & Upjohn), and those cDNAs exceeding 400 bp are ligated into pINCY I. The plasmid pINCY I is subsequently transformed into DH5 alpha TM competent cells (Cat. #18258-012, Gibco BRL).

EXAMPLE 2

Isolation and Sequencing of cDNA Clones

Plasmid DNA is released from the cells and purified using the REAL Prep 96 Plasmid kit (Catalog #26173, QIAGEN, Inc.). The recommended protocol is employed except for the following changes: 1) the bacteria are cultured in 1 ml of sterile Terrific Broth (Catalog #22711, LIFE TECHNOLOGIES™, Gaithersburg, Md.) with carbenicillin at 25 mg/L and glycerol at 0.4%; 2) after inoculation, the cultures are incubated for 19 hours and at the end of incubation, the cells are lysed with 0.3 ml of lysis buffer; and 3) following isopropanol precipitation, the plasmid DNA pellet is resuspended in 0.1 ml of distilled water. After the last step in the protocol, samples are transferred to a 96-well block for storage at 4° C.

The cDNAs are sequenced by the Sanger method using a Hamilton Micro Lab 2200 (Hamilton) in combination with Peltier Thermal Cyclers PTC200 (MJ Research) and Applied Biosystems 377 DNA Sequencing Systems; and the reading frame is determined.

EXAMPLE 3

Homology Searching of cDNA Clones and Their Deduced Proteins

Each cDNA is compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) is used to determine regions of homology. The three parameters that determine how the sequence comparisons run are window size, window offset, and error tolerance. Using a combination of these three parameters, the DNA database is searched for sequences containing regions of homology to the query sequence, and the appropriate sequences are scored with an initial value. Subsequently, these homologous regions are examined using dot matrix homology plots to distinguish regions of homology from chance matches. Smith-Waterman alignments are used to display the results of the homology search.

Peptide and protein sequence homologies are ascertained using the INHERIT™ 670 sequence analysis system using the methods similar to those used in DNA sequence homologies. Pattern Specification Language and parameter windows are used to search protein databases for sequences containing regions of homology which are scored with an initial value. Dot-matrix homology plots are examined to distinguish regions of significant homology from chance matches.

BLAST is used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting. database sequence matches. E is interpreted as the upper bound of the expected frequency of chance occurrence of an HSP (or set of HSPs) within the context of the entire database search. Any database sequence whose match satisfies E is reported in the program output.

EXAMPLE 4

Northern Blot Analysis

Northern blot analysis is a laboratory technique used to detect the presence of a transcript of a gene and involves the hybridization of a labeled nucleotide sequence to a membrane on which RNAs from a particular cell type or tissue have been bound.

Analogous computer techniques using BLAST are used to search for identical or related molecules in nucleotide databases such as GenBank or the LIFESEQ™ (human gene database) database (Incyte Pharmaceuticals). This analysis is much faster than multiple, membrane-based hybridizations. In addition, the sensitivity of the computer search can be modified to determine whether any particular match is categorized as exact or homologous. The basis of the search is the product score which is defined as: (% sequence identity x % maximum BLAST score)/100.

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of Northern blot analysis are reported as a list of libraries in which the transcript encoding Aven occurs. Abundance and percent abundance are also reported. Abundance directly reflects the number of times a particular transcript is represented in a cDNA library, and percent abundance is abundance divided by the total number of sequences examined in the cDNA library.

EXAMPLE 5

Extension of Aven-Encoding Polynucleotides to Full Length or to Recover Regulatory Sequences Full length Aven-encoding nucleic acid sequence (FIG. 2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward", generating amplicons containing new, unknown nucleotide sequence for the region of interest. The initial primers are designed from the cDNA using OLIGO 4.06 (primer analysis software) (National Biosciences, Plymouth, Mich.), or another appropriate program, to be 22–30 nucleotides in length, to have a GC content of 50% or more, and to anneal to the target sequence at temperatures about 68–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler PTC200 and the following parameters:

| Step 1 | 94° C. for 1 min (initial denaturation) |
| --- | --- |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK™ (PCR purification kit, QIAGEN Inc.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium. After incubation for one hour at 37° C., the whole transformation mixture is plated on LB agar containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

EXAMPLE 6

Labeling and Use of Hybridization Probes

Hybridization probes derived from the nucleotide sequence shown in FIG. 2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (primer analysis software) (National Biosciences), labeled by combining 50 pmol of each oligomer and 250 $\mu$Ci of $\gamma$-$^{32}$P adenosine triphosphate (Amersham) and NEN™ T4 polynucleotide kinase (DuPont, Boston, Mass.). The labeled oligonucleotides are substantially purified with SEPHADEX G-25 superfine resin column (purification reagents) (Pharmacia & Upjohn). A portion containing $10^7$ counts per minute of each of the sense and antisense oligonucleotides is used in a typical membrane based hybridization analysis of human genomic DNA digested with one of the following endonucleases (AseI, BglII, EcoRI, PstI, XbaI, or PvuII; DuPont NEN™).

The DNA from each digest is fractionated on a 0.7 percent agarose gel and transferred to NYTRAN PLUS nylon membranes (nylon transfer membrane) (Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ (x-ray film developing processor) film (Kodak, Rochester, N.Y.) is exposed to the blots, or the blots are exposed to Phosphoimager cassette (Molecular Dynamics, Sunnyvale, Calif.) for several hours, hybridization patterns are compared visually.

EXAMPLE 7

Antisense Molecules

Antisense molecules to the Aven-encoding sequence, or any part thereof, is used to inhibit in vivo or in vitro expression of naturally occurring Aven. Although use of antisense oligonucleotides, comprising about 20 base-pairs, is specifically described, essentially the same procedure is used with larger cDNA fragments. An oligonucleotide based on the coding sequences of Aven, as shown in FIG. 2 (SEQ ID NO: 1), is used to inhibit expression of naturally occurring Aven. The complementary oligonucleotide is designed from the most unique 5' sequence as shown in FIG. 2 and used either to inhibit transcription by preventing promoter binding to the upstream nontranslated sequence or translation of an Aven-encoding transcript by preventing the ribosome from binding. Using an appropriate portion of the signal and 5' sequence of FIG. 2, an effective antisense oligonucleotide includes any 15–20 nucleotides spanning the region which translates into the signal or 5' coding sequence of the polypeptide.

EXAMPLE 8

Expression of Aven

Expression of Aven is accomplished by subcloning the cDNAs into appropriate vectors and transforming the vectors into host cells. In this case, the cloning vector, PSPORT, which is used for the generation of the cDNA library is also used to express Aven in *E. coli*. Upstream of the cloning site, this vector contains a promoter for beta-galactosidase, followed by sequence containing the amino-terminal Met, and the subsequent seven residues of beta-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of beta-galactosidase, about 5 to 15 residues of linker, and the full length protein. The signal residues direct the secretion of Aven into the bacterial growth media which can be used directly in the following assay for activity.

EXAMPLE 9

Demonstration of Aven Activity

Aven activity can be assayed in BHK cells seeded on a microscope slide and transiently transfected with the following plasmids: one which contains the nucleic acid sequence encoding Aven and one which contains tandemly arranged coding sequences for tumor necrosis factor alpha (TNF-alpha, which causes apoptosis) and beta-galactosidase. The cells are fixed after twelve hours and incubated in a buffer containing X-gal to visualize beta-galactosidase activity. Phase or interference contrast microscopy is used to examine the slides. Cells expressing only the plasmid with TNF-alpha display shrunken nuclei, intense blue staining and membrane blebbing. Cells expressing both plasmids show nearly normal nuclei, intense blue staining, and nearly normal membranes, no blebbing.

EXAMPLE 10

Production of Aven Specific Antibodies

Aven that is substantially purified using PAGE electrophoresis or other purification techniques, is used to immunize rabbits and to produce antibodies using standard protocols. The amino acid sequence deduced from FIG. 2 is analyzed using DNASTAR software (sequence analysis software) (DNASTAR Inc.) to determine regions of high immunogenicity and a corresponding oligopolypeptide is synthesized and used to raise antibodies by means known to those of skill in the art. Selection of appropriate epitopes, which may be those near the C-terminus or in hydrophilic regions, is then performed.

Typically, the oligopeptides are 15 residues in length, synthesized using an Applied Biosystems Peptide Synthesizer Model 431A using fmoc-chemistry, and coupled to keyhole limpet hemocyanin (KLH) (Sigma, St. Louis, Mo.) by reaction with N-maleimidobenzoyl-N-hydroxysuccinimide ester (MBS). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

EXAMPLE 11

Purification of Naturally Occurring Aven Using Specific Antibodies

Naturally occurring or recombinant Aven is substantially purified by immunoaffinity chromatography using antibodies specific for Aven. An immunoaffinity column is constructed by covalently coupling Aven antibody to an activated chromatographic resin, such as CnBr-activated SEPHAROSE (agarose beads) (Pharmacia & Upjohn). After the coupling, the resin is blocked and washed according to the manufacturer's instructions.

Media containing Aven is passed over the immunoaffinity column, and l0 the column is washed under conditions that allow the preferential absorbance of Aven (e.g., high ionic strength buffers in the presence of detergent). The column is eluted under conditions that disrupt antibody/Aven binding (e.g., a buffer of pH 2–3 or a high concentration of a chaotropc, such as urea or thiocyanate ion), and Aven is collected.

EXAMPLE 12

Identification of Molecules Which Interact with Aven

Aven or biologically active fragments thereof are labeled with $^{125}$I Bolton-Hunter reagent. Candidate molecules previously arrayed in the wells of a multi-well plate are incubated with the labeled Aven, washed and any wells with labeled Aven complex are assayed. Data obtained using different concentrations of Aven are used to calculate values for the number, affinity, and association of Aven with the candidate molecules.

Other methods of identifying molecules which interact with Aven include Western blotting, immunoprecipitation, co-immunoprecipitation, one-hybrid systems, and two-hybrid systems. Suitable one-hybrid systems include the MATCHMAKER One-Hybrid System (yeast one-hybrid system) (Clontech), which detects DNA-protein interactions, and suitable two-hybrid systems include the MATCHMAKER LexA Two-Hybrid System (Clontech) and the MATCHMAKER GAL4 Two-Hybrid System (Clontech) for detecting protein-protein interactions in yeast, and the mammalian MATCHMAIER Two-Hybrid System (Clontech) for detecting protein-protein interactions in mammalian cells.

EXAMPLE 13

Aven-induced Protection Against Sindbis Virus Infection and Neuronal Apoptosis In Vivo Three-day-old CD-1 mice were inoculated by intracerebral injection with a control Sindbis virus encoding bacterial chloramphenicol acetyltransferase (CAT) or with Sindbis virus encoding HA-Aven and monitored for 21 days. Percent survival for groups consisting of forty mice per group were determined as shown in FIG. 11. The data demonstrated that Aven exhibits a protective function against neuronal apoptosis in vivo.

EXAMPLE 14

Viability of Cells Stably Transfected With Aven In Vitro

The viability of FL5.12 cells stably transfected with Aven or with empty vector was determined by trypan blue exclusion at various time intervals after resuspension in IL-3-deficient medium (FIGS. 12A and B). The data was collected and demonstrated than Aven increased resistance to apoptosis induced by IL-3 withdrawal.

EXAMPLE 15

Viability of BHK Cells Transfected With Aven

BHK cells were transfected with the indicated constructs plus a GAL plasmid to mark transfected cells (FIG. 13). Empty vector was included so that all cells received equivalent amounts of DNA. Percent viability was determined as the percentage of viable blue cells, as shown in FIG. 13. The data demonstrated that Aven enhances the anti-apoptotic activity of Bcl-xL.

EXAMPLE 16

Increasing the Yield of Recombinant Protein Expression In A Host Cell Line

A Host Cell Line was stably transfected with a vector capable of expressing Aven or a biologically active fragment of Aven under the control of an inducible promoter. A second vector capable of expressing a recombinant protein of interest is introduced into the cell line stably transfected with the Aven vector ("the Aven cell line"). The recombinant protein encoded by the second vector is expressed in the Aven cell line and collected.

EXAMPLE 17

Aven Inhibits Self-association of Apaf-1

A construct expressing the N-terminal 455 amino acids of Apaf-1 containing both CED-3 and CED-4 homology domains (HA-Apaf1–3+4) was co-transfected with full length Apaf-1 with or without Aven (FIG. 14A). Co-immunoprecipitated Apaf-1 as described in FIG. 14A was quantitated by densitometry of autoradiographs and presented as relative units (FIG. 14B).

EXAMPLE 18

Aven Inhibits the Activation of Caspases by Cytochrome c and dATP in Cell Extracts Extracts were prepared from 293T cells transfected with Aven or vector alone and incubated with DATP for various time intervals prior to immunoblot analysis for endogenous caspase-9 (in panel C) or endogenous caspase-3 (in panel D) (FIGS. 15A–D). The proforms and cleavage products are marked by arrows.

EXAMPLE 19

Aven Increases The Viability of CHO Cells

Aven, Aven-reverse, CAT and a mock control were stably expressed in CHO cells. Aven increases the viability of CHO cells in vitro by approximately 20% (FIG. 16).

EXAMPLE 20

Aven Interacts With Bcl-2 Family Members

Yeast two-hybrid and co-immunoprecipitation analyses were performed on COS-1 cell lysates demonstrating the ability of Aven to interact with other Bcl-2 family members. The constructs included in the transfection are indicated as a (+) (FIGS. 6, 7, and 8). The immunoprecipitating antibodies (top) and immunoblotting antibodies (side) are indicated (FIGS. 7 and 8).

EXAMPLE 21

Aven And Apaf-1 Interact

Apaf-1 and Aven were co-transfected into COS-1 cells with HA-Aven or HA-ΔN73 Aven in the presence or absence of Bcl-xL. Total cell lysates or anti-HA immunoprecipitates were immunoblotted with the indicated antibodies. Endogenous Bcl-xL in both transfected and untransfected cells was also detected with the anti-Bcl-xL antibody (FIG. 9A).

Lysates and anti-Aven-b immunoprecipitates of cells were co-transfected with HA-Apaf-1 and HA-wt- or ΔN73-Aven and immunoblotted with anti-HA antibody (FIG. 9B).

Hela cell extracts were immunoprecipitated with pre- or post-immune Aven-a antiserum and immunoblotted with a polyclonal antibody to Apaf-1 (provided by X. Wang)(FIG. 9D).

293T cell extracts were immunoprecipitated with pre- or post-immune Aven-b antiserum and immunoblotted with a monoclonal antibody to Apaf-1 (provided by Y. Lazebnik) (FIG. 9E).

EXAMPLE 22

Aven Interacts With Apaf-1 Independently of Bcl-xL

Co-immunoprecipitation experiments were performed on transfected cells as described in Example 21 above (FIGS. 9F–J). The data demonstrated that Aven interacts with Apaf-1 independently of Bcl-xL.

All publications and patents mentioned in the above specification are herein incorporated by reference. The above description, drawings and examples are only illustrative of preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed is:

1. An isolated DNA sequence encoding a substantially purified protein comprising the amino acid sequence of SEQ ID NO:2.

2. An isolated DNA sequence encoding a fragment of the amino acid sequence of SEQ ID NO: 2, said fragment comprising the carboxy terminus of SEQ ID NO: 2 and being capable of inhibiting apoptosis.

3. The DNA sequence of claim 2 wherein said DNA is operatively linked to at least one control sequence.

4. A vector comprising the DNA of claim 3 wherein said vector is capable of expressing a protein encoded by said DNA.

5. A host cell transformed with a vector comprising the isolated DNA sequence of claim 2, wherein said host cell is capable of expressing a protein encoded by the DNA of said vector.

6. A host cell stably transformed with a vector comprising the isolated DNA sequence of claim 2, wherein said host cell is capable of expressing a protein encoded by the DNA of said vector.

7. A substantially purified nucleic acid compound comprising the DNA sequence of FIG. 2 (SEQ ID NO: 1).

8. An isolated nucleic acid encoding a fragment of the amino acid sequence of SEQ ID NO: 2, said fragment comprising the carboxy terminus of SEQ ID NO: 2 and being capable of inhibiting apoptosis.

* * * * *

SEQUENCE LISTING

<160> NUMBER OF SEQ ID NOS: 3

<210> SEQ ID NO 1
<211> LENGTH: 1566
<212> TYPE: DNA
<213> ORGANISM: Homo sapiens
<220> FEATURE:
<221> NAME/KEY: CDS
<222> LOCATION: (53)..(1138)
<221> NAME/KEY: modified_base
<222> LOCATION: (1533)..(1534)
<223> OTHER INFORMATION: a, t, c, g, other or unknown

<400> SEQUENCE: 1

```
gggcgtctcc gcagctcggc tcccgcgcgc tcagcaccac cagcggcgcc ag atg cag        58
                                                          Met Gln
                                                            1 gcg gag cga gga gct cgg gga ggc cgt ggg cgg cgg cca ggc cgc ggc         106
Ala Glu Arg Gly Ala Arg Gly Gly Arg Gly Arg Arg Pro Gly Arg Gly
        5                   10                  15 cgg cct ggc gga gat cgc cac agc gag cgg ccc gga gcc gca gcg gcg        154
Arg Pro Gly Gly Asp Arg His Ser Glu Arg Pro Gly Ala Ala Ala Ala
20                  25                  30 gta gcc aga ggc ggc ggc gga ggc ggc ggc ggg gac gga ggc gga cgc        202
Val Ala Arg Gly Gly Gly Gly Gly Gly Gly Gly Asp Gly Gly Gly Arg
35                  40                  45                  50 cgg ggc cgt ggc cgt ggc cgg ggc ttc cgc ggc gct cgc gga ggc cga        250
Arg Gly Arg Gly Arg Gly Arg Gly Phe Arg Gly Ala Arg Gly Gly Arg
                55                  60                  65 gga gga gga ggc gcc ccg cga ggc agc cgc cgg gag ccg gga ggc tgg        298
Gly Gly Gly Gly Ala Pro Arg Gly Ser Arg Arg Glu Pro Gly Gly Trp
            70                  75                  80 ggc gca ggg gcc agc gcg ccg gtt gaa gat gac agc gat gca gag acc        346
Gly Ala Gly Ala Ser Ala Pro Val Glu Asp Asp Ser Asp Ala Glu Thr
        85                  90                  95 tat gga gaa gag aat gat gaa cag gga aat tat tct aaa aga aag att        394
Tyr Gly Glu Glu Asn Asp Glu Gln Gly Asn Tyr Ser Lys Arg Lys Ile
100                 105                 110 gtc tct aac tgg gat cga tat caa gat att gaa aaa gag gtc aat aat        442
Val Ser Asn Trp Asp Arg Tyr Gln Asp Ile Glu Lys Glu Val Asn Asn
115                 120                 125                 130 gaa agt gga gag tca cag agg gga aca gat ttc agt gtc ctc ctt agc        490
Glu Ser Gly Glu Ser Gln Arg Gly Thr Asp Phe Ser Val Leu Leu Ser
                135                 140                 145 tct gca ggg gac tca ttc tca cag ttc cgg ttt gct gag gag aaa gaa        538
Ser Ala Gly Asp Ser Phe Ser Gln Phe Arg Phe Ala Glu Glu Lys Glu
            150                 155                 160 tgg gat agt gaa gct tct tgt cca aaa cag aat tca gca ttt tat gtg        586
Trp Asp Ser Glu Ala Ser Cys Pro Lys Gln Asn Ser Ala Phe Tyr Val
        165                 170                 175 gat agt gag tta ttg gtt cga gcc ctt caa gag ctg cct ctc tgc ctc        634
Asp Ser Glu Leu Leu Val Arg Ala Leu Gln Glu Leu Pro Leu Cys Leu
    180                 185                 190 cga ctc aac gtt gct gcc gaa ctg gtc cag ggt aca gtt cct tta gag        682
Arg Leu Asn Val Ala Ala Glu Leu Val Gln Gly Thr Val Pro Leu Glu
195                 200                 205                 210 gtt cct cag gtg aaa cca aag aga act gat gat ggc aag gga tta ggg        730
Val Pro Gln Val Lys Pro Lys Arg Thr Asp Asp Gly Lys Gly Leu Gly
                215                 220                 225 atg cag tta aag ggg ccc ttg ggg cct gga gga agg ggg ccc atc ttt        778
```

```
Met Gln Leu Lys Gly Pro Leu Gly Pro Gly Gly Arg Gly Pro Ile Phe
            230                 235                 240 gag ctg aaa tct gtg gct gct ggc tgc cct gtg ttg ctg ggc aaa gac    826
Glu Leu Lys Ser Val Ala Ala Gly Cys Pro Val Leu Leu Gly Lys Asp
            245                 250                 255 aac cca agc ccg ggt cct tca agg gat tct cag aaa ccc act tcc cca    874
Asn Pro Ser Pro Gly Pro Ser Arg Asp Ser Gln Lys Pro Thr Ser Pro
        260                 265                 270 ctg cag tca gca gga gac cat ttg gaa gaa gaa cta gat ctg ttg ctt    922
Leu Gln Ser Ala Gly Asp His Leu Glu Glu Glu Leu Asp Leu Leu Leu
275                 280                 285                 290 aat tta gat gca cct ata aaa gag gga gat aac atc tta cca gat cag    970
Asn Leu Asp Ala Pro Ile Lys Glu Gly Asp Asn Ile Leu Pro Asp Gln
                295                 300                 305 acg tct cag gac ctg aaa tcc aag gaa gat ggg gag gtg gtc caa gag   1018
Thr Ser Gln Asp Leu Lys Ser Lys Glu Asp Gly Glu Val Val Gln Glu
            310                 315                 320 gaa gaa gtt tgt gca aaa cca tct gtg act gaa gaa aaa aac atg gaa   1066
Glu Glu Val Cys Ala Lys Pro Ser Val Thr Glu Glu Lys Asn Met Glu
            325                 330                 335 cct gag caa cca agt acc tcc aaa aat gtt acc gag gaa gag ctg gaa   1114
Pro Glu Gln Pro Ser Thr Ser Lys Asn Val Thr Glu Glu Glu Leu Glu
        340                 345                 350 gac tgg ttg gac agc atg att tcc taaaagggg gaaaaagtg cctgaagcaa    1168
Asp Trp Leu Asp Ser Met Ile Ser
355                 360 atcttggttg ccttctaacg gcaggtgggc ataaggctgt ccttcaggac cagccagttt    1228
acaagcatgt ctcaagctag tgtgttccat tatgctcaca gcagtaaatg cctacctctg    1288
tgtttgacat ctgaaagaat acattgaagc agcttgttgc atttgttttt ctggcttagt    1348
aatctaatag atttccttaa gggcaggaga tagactctgg cccttgtttc tagcctcctt    1408
ccttgcagtg tttacaacat agccagtgtt tacagcatag cagatgctgc tgctggttaa    1468
gagaatagat gcaaacaagg catgcatttg gccaaaataa acaaatgctg gtctgtccaa    1528 aaaanaaaa aaaaaaaaaa aggccttcgt ggcctcga                             1566

<210> SEQ ID NO 2
<211> LENGTH: 362
<212> TYPE: PRT
<213> ORGANISM: Homo sapiens

<400> SEQUENCE: 2

Met Gln Ala Glu Arg Gly Ala Arg Gly Gly Arg Gly Arg Pro Gly
 1               5                  10                  15

Arg Gly Arg Pro Gly Gly Asp Arg His Ser Glu Arg Pro Gly Ala Ala
                20                  25                  30

Ala Ala Val Ala Arg Gly Gly Gly Gly Gly Gly Asp Gly Gly
            35                  40                  45

Gly Arg Arg Gly Arg Gly Arg Gly Arg Gly Phe Arg Gly Ala Arg Gly
        50                  55                  60

Gly Arg Gly Gly Gly Ala Pro Arg Gly Ser Arg Arg Glu Pro Gly
65                  70                  75                  80

Gly Trp Gly Ala Gly Ala Ser Ala Pro Val Glu Asp Asp Ser Asp Ala
                85                  90                  95

Glu Thr Tyr Gly Glu Glu Asn Asp Glu Gln Gly Asn Tyr Ser Lys Arg
            100                 105                 110

Lys Ile Val Ser Asn Trp Asp Arg Tyr Gln Asp Ile Glu Lys Glu Val
```

-continued

```
                115                 120                 125
Asn Asn Glu Ser Gly Glu Ser Gln Arg Gly Thr Asp Phe Ser Val Leu
    130                 135                 140

Leu Ser Ser Ala Gly Asp Ser Phe Ser Gln Phe Arg Phe Ala Glu Glu
145                 150                 155                 160

Lys Glu Trp Asp Ser Glu Ala Ser Cys Pro Lys Gln Asn Ser Ala Phe
                165                 170                 175

Tyr Val Asp Ser Glu Leu Leu Val Arg Ala Leu Gln Glu Leu Pro Leu
                180                 185                 190

Cys Leu Arg Leu Asn Val Ala Ala Glu Leu Val Gln Gly Thr Val Pro
            195                 200                 205

Leu Glu Val Pro Gln Val Lys Pro Lys Arg Thr Asp Asp Gly Lys Gly
    210                 215                 220

Leu Gly Met Gln Leu Lys Gly Pro Leu Gly Pro Gly Gly Arg Gly Pro
225                 230                 235                 240

Ile Phe Glu Leu Lys Ser Val Ala Ala Gly Cys Pro Val Leu Leu Gly
                245                 250                 255

Lys Asp Asn Pro Ser Pro Gly Pro Ser Arg Asp Ser Gln Lys Pro Thr
                260                 265                 270

Ser Pro Leu Gln Ser Ala Gly Asp His Leu Glu Glu Glu Leu Asp Leu
            275                 280                 285

Leu Leu Asn Leu Asp Ala Pro Ile Lys Glu Gly Asp Asn Ile Leu Pro
    290                 295                 300

Asp Gln Thr Ser Gln Asp Leu Lys Ser Lys Glu Asp Gly Glu Val Val
305                 310                 315                 320

Gln Glu Glu Glu Val Cys Ala Lys Pro Ser Val Thr Glu Glu Lys Asn
                325                 330                 335

Met Glu Pro Glu Gln Pro Ser Thr Ser Lys Asn Val Thr Glu Glu Glu
            340                 345                 350

Leu Glu Asp Trp Leu Asp Ser Met Ile Ser
        355                 360

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 3
cggaattccg                                                              10
```